United States Patent
Ge

(10) Patent No.: US 9,453,003 B2
(45) Date of Patent: *Sep. 27, 2016

(54) PYRIMIDINE DERIVATIVES AS PIM KINASE INHIBITORS AND PREPARATION METHODS AND USE IN MEDICINAL MANUFACTURE THEREOF

(71) Applicant: Jikai Biosciences, Inc., Shanghai (CN)

(72) Inventor: Yu Ge, Shanghai (CN)

(73) Assignee: Jikai Biosciences, Inc., Shanghai (CN)

(*) Notice: Subject to any disclaimer, the term of this patent is extended or adjusted under 35 U.S.C. 154(b) by 0 days.

This patent is subject to a terminal disclaimer.

(21) Appl. No.: 14/746,638

(22) Filed: Jun. 22, 2015

(65) Prior Publication Data

US 2015/0284373 A1    Oct. 8, 2015

Related U.S. Application Data

(63) Continuation-in-part of application No. 14/177,156, filed on Feb. 10, 2014, now Pat. No. 9,090,594, and a continuation of application No. PCT/CN2012/001060, filed on Aug. 8, 2012.

(30) Foreign Application Priority Data

Aug. 11, 2011   (CN) .......................... 2011 1 0229731
Aug. 1, 2012    (CN) .......................... 2012 1 0271738

(51) Int. Cl.
| | | |
|---|---|---|
| A61K 31/506 | (2006.01) |
| C07D 405/14 | (2006.01) |
| C07D 401/14 | (2006.01) |
| C07D 401/12 | (2006.01) |
| C07D 413/14 | (2006.01) |
| C07D 403/14 | (2006.01) |
| C07D 417/12 | (2006.01) |
| C07D 417/14 | (2006.01) |
| C07D 451/02 | (2006.01) |
| C07D 451/06 | (2006.01) |
| C07D 453/02 | (2006.01) |
| C07D 471/08 | (2006.01) |
| C07D 487/08 | (2006.01) |
| C07D 403/02 | (2006.01) |
| C07D 413/12 | (2006.01) |

(52) U.S. Cl.
CPC ........... *C07D 405/14* (2013.01); *C07D 401/12* (2013.01); *C07D 401/14* (2013.01); *C07D 403/14* (2013.01); *C07D 413/14* (2013.01); *C07D 417/12* (2013.01); *C07D 417/14* (2013.01); *C07D 451/02* (2013.01); *C07D 451/06* (2013.01); *C07D 453/02* (2013.01); *C07D 471/08* (2013.01); *C07D 487/08* (2013.01); *A61K 31/506* (2013.01); *C07D 403/02* (2013.01); *C07D 413/12* (2013.01)

(58) Field of Classification Search
CPC ........................... C07D 401/12; C07D 401/14
See application file for complete search history.

(56) References Cited

U.S. PATENT DOCUMENTS

| | | | |
|---|---|---|---|
| 4,332,809 A | 6/1982 | Honma et al. | |
| 4,879,295 A | 11/1989 | Yoshinaga et al. | |
| 8,329,732 B2 * | 12/2012 | Burger ................ | C07D 401/12 514/332 |
| 8,592,455 B2 * | 11/2013 | Burger ................ | C07D 401/12 514/318 |
| 8,969,584 B2 * | 3/2015 | Ge ....................... | C07D 417/12 548/214 |
| 8,987,457 B2 * | 3/2015 | Burger ................ | C07D 403/12 546/193 |
| 9,079,889 B2 * | 7/2015 | Burger ................ | C07D 401/12 |
| 9,090,594 B2 * | 7/2015 | Ge ....................... | C07D 417/12 |
| 2010/0056576 A1 * | 3/2010 | Burger ................ | C07D 401/12 514/332 |
| 2011/0044940 A1 | 2/2011 | Shipps, Jr. et al. | |

(Continued)

FOREIGN PATENT DOCUMENTS

WO    WO 2008/106692 A1    9/2008
WO    WO 2008/141976 A1    11/2008

(Continued)

OTHER PUBLICATIONS

Chemotherapy of Neoplastic Diseases in, Goodman & Gilman's: The Pharmacological Basis of Therapeutics 853-908 (L.L. Brunton et al., eds., 11th ed., 2008).*

(Continued)

*Primary Examiner* — Alexander R Pagano
(74) *Attorney, Agent, or Firm* — Mei & Mark LLP; Manni Li

(57) ABSTRACT

PIM kinase inhibitor compound having a structure as represented by Formula I, and isomers, diastereomers, enantiomers, tautomers, and pharmaceutically acceptable salts thereof. The compounds significantly inhibit the Pim kinase activity and are used to prepare drugs to treat PIM kinase mediated diseases, such as cancers, multi drug resistance, and inflammatory bowel disease. Also provided are methods for preparing and using the compounds represented by Formula I.

I

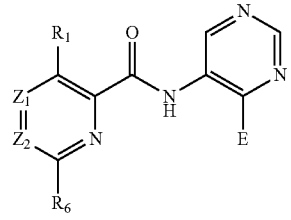

14 Claims, No Drawings

(56) References Cited

U.S. PATENT DOCUMENTS

| | | | | |
|---|---|---|---|---|
| 2012/0134987 | A1* | 5/2012 | Burger | C07D 401/12 424/133.1 |
| 2012/0225061 | A1* | 9/2012 | Burger | A61K 31/444 424/133.1 |
| 2013/0336965 | A1* | 12/2013 | Burger | C07D 403/12 424/133.1 |
| 2014/0079693 | A1* | 3/2014 | Burger | C07D 401/12 424/133.1 |
| 2014/0162998 | A1* | 6/2014 | Ge | C07D 417/12 514/210.2 |
| 2014/0162999 | A1* | 6/2014 | Ge | C07D 417/12 514/210.2 |
| 2014/0200216 | A1* | 7/2014 | Li | C07D 491/048 514/235.2 |
| 2014/0228363 | A1* | 8/2014 | Burger | A61K 31/444 514/235.5 |
| 2014/0249135 | A1* | 9/2014 | Burger | C07D 401/12 514/211.15 |
| 2015/0133473 | A1* | 5/2015 | Burger | C07D 403/12 514/256 |
| 2015/0150873 | A1* | 6/2015 | Burger | C07D 403/12 514/256 |
| 2015/0284363 | A1* | 10/2015 | Ge | C07D 401/12 514/210.2 |
| 2015/0284378 | A1* | 10/2015 | Ge | C07D 417/12 514/210.2 |
| 2015/0315150 | A1* | 11/2015 | Burger | C07D 401/12 424/133.1 |

FOREIGN PATENT DOCUMENTS

| | | | | |
|---|---|---|---|---|
| WO | WO 2008141976 | A1 * | 11/2008 | |
| WO | WO 2010/078408 | A1 | 7/2010 | |
| WO | WO 2013020370 | A1 * | 2/2013 | C07D 401/14 |

OTHER PUBLICATIONS

C. Fuji et al., 114 International Journal of Cancer, 209-218 (2005).*
T. Morwick, 20 Expert Opinion on Therapeutic Patents, 193-212 (2010).*
V. Pogacic et al., 67 Cancer Research, 6916-6924 (2007).*
U.S. Appl. No. 14/746,720, Ge, Yu, Jun. 22, 2015, copending application.
U.S. Appl. No. 14/746,773, Ge, Yu, Jun. 22, 2015, copending application.
Marius Vantler et al., "Systematic Evaluation of Anti-Apoptotic Growth Factor Signaling in Vascular Smooth Muscle Cells," The Journal of Biological Chemistry, vol. 280, No. 14, pp. 14168-14176 (Issue of Apr. 8, 2005).
Peter S. Hammerman et al., "Pim and Akt oncogenes are independent regulators of hemotopoietic cell growth and survival," Blood, vol. 105, No. 11, pp. 4477-4483 (Jun. 1, 2005).
Casey J. Fox et al., "The Pim kinases control rapamycin-resistant T cell survival and activation," The Journal of Experimental Medicine, vol. 201, No. 2, pp. 259-266 (Juanuary 17, 2005).
D.A. Fruman, "Towards an understanding of isoform specificity in phosphoinositide 3-kinase signalling in lymphocytes," Biochem. Soc. Trans. vol. 32, pp. 315-319 (2004).
H. Theo Cuypers et al., "Murine leukemia virus-induced T-cell lymphomagenesis: integration of proviruses in a distrinct chromosomal region," Cell, vol. 37, pp. 141-150 (May 1984).
Beth Levine et al., "Autophagy in cell death: an innocent convict?" The Journal of Clinical Investigation, vol. 115, No. 10, pp. 2679-2688 (Oct. 2005).
Nathalie M. T. Van Der Lugt et al., "Proviral tagging in Eµ-*myc* transgenic mice lacking the *Pim*-1 proto-oncogene leads to compensatory activation of *Pim*-2," The EMBO Journal, vol. 14, No. 11, pp. 2536-2544 (1995).
Hans-Guido Wendel et al., "Survival signalling by Akt and eIF4E in oncogenesis and cancer therapy," Nature, 428, pp. 332-337 (Mar. 18, 2004).

Maarten Van Lohuizen et al., "Predisposition to lymphomagenesis in *pim*-1 transgenic mice: Cooperation with c-*myc* and N-*myc* in murine leukemia virus-induced tumors," Cell 56, Issue 4, pp. 673-682 (Feb. 24, 1989).
Robert Amson et al., "The human protooncogene product p33pim is expressed during fetal hematopoiesis and in diverse leukemias," Proc. Natl. Acad. Sci. USA, vol. 86, pp. 8857-8861 (Nov. 1989).
T.L. Cibull et al., "Overexpression of Pim-1 during progression of prostatic adenocarcinoma," J. Clin. Pathol., vol. 59, pp. 285-288 (2006).
Amos M. Cohen et al., "Increased Expression of the hPim-2 gene in human chronic lymphocytic leukemia and non-Hodgkin lymphoma," Leuk. Lymph., 45, pp. 951-955 (2004).
Chifumi Fujii et al., "Aberrant expression of serine/threonine kinase Pim-3 in hepatocellular carcinoma development and its role in the proliferation of human hepatoma cell lines," Int. J. Cancer, vol. 114, pp. 209-218 (2005).
Ying-Yi Li et al., "Pim-3, a proto-oncogene with serine/threonine kinase activity, is aberrantly expressed in human pancreatic cancer and phosphorylates bad to block bad-mediated apoptosis in human pancreatic cancer cell lines," Cancer Res., vol. 66, pp. 6741-6747 (Jul. 1, 2006).
Teija L.T. Aho et al., "Pim-1 kinase promotes inactivation of the pro-apoptotic bad protein by phosphorylating it on the $Ser^{112}$ gatekeeper site," FEBS Letters, vol. 571, pp. 43-49 (2004).
Zeping Wang et al., "Phosphorylation of the cell cycle inhibitor $p21^{Cip1/WAF1}$ by Pim-1 kinase," Biochem. Biophys. Acta, vol. 1593, pp. 45-55 (2002).
Malte Bachmann et al., "The oncogenic serine/threonine kinase Pim-1 phosphorylates and inhibits the activity of Cdc25C-associated kinase 1 (C-TAK1)," The Journal of Biological Chemistry, vol. 279, No. 46, pp. 48319-48328 (Issue of Nov. 12, 2004).
Teija L. T. Aho et al., "Expression of human *pim* family genes is selectively up-regulated by cytokines promoting T helper type 1, but not T helper type 2, cell differentiation," Immunology, vol. 116, pp. 82-88 (2005).
L.L. Brunton et al., Chemotherapy of Neoplastic Diseases in, Goodman & Gilman's: The Pharmacological Basis of Therapeutics 853-908 (eds., 11th ed., 2008).
P. Garcia et al., Pan-PIM Kinase Inhibition Provides a Novel Therapy for Treating Hematologic Cancers, Clin. Cancer Res. 20(7), 1834-1845, 2014.
E. Keeton et al., AZD1208, a potent and selective pan-Pim kinase inhibitor, demonstrates efficacy in preclinical models of acute myeloid leukemia, Blood 123(6), 905-913, 2014.
T. Paino et al., Dual Antitumoral and Bone Antiresorptive Effect of the Pan-Pim Kinase inhibitor, LGH447, in multiple myeloma, Blood 122(21), 4435, 2013.
Carolin Reiser-Erkanet al., Hypoxia-inducible proto-oncogene Pim-1 is a prognostic marker in pancreatic ductal adenocarcinoma, Cancer Biology & Therapy, 7:9, 1352-1359(2008).
Adam Siddiqui-Jain et al., CX-4945, an Orally Bioavailable Selective Inhibitor of Protein Kinase CK2, Inhibits Prosurvival and Angiogenic Signaling and Exhibits Antitumor Efficacy, Cancer Res. 70(24), 10288-10298, 2010.
H. Dai et al., Pim-2Upregulation:Biological Implications Associated With Disease Progression and Perinueral Invasionin Prostate Cancer, Prostate, 65(3), 276- 86, 2005.
K. Ren et al., Over-Expression of Pim-2 Promote theTumorigenesis of Prostatic Carcinoma Through Phosphorylating eIF4B , Prostate, 73(13), 1462-1469, 2013.
J. Gong et al., Serine/Threonine Kinase Pim-2 Promotes Liver Tumorigenesis induction Through Mediating Survival and Preventing Apoptosis of Liver Cell, J. Surg. Res., 153(1), 17-22, 2009.
H. Zheng et al., Aberrant Pim-3 expression is involved in gastric adenoma-adenocarcinoma sequence and cancer progression, J. Cancer Res. Clin. Oncol., 134(4), 481-8, 2008.
S. Guo et al., Overexpression of Pim-1 in bladder cancer, J. Exp. Clin. Cancer Res., 29, 161, 2010.

(56) References Cited

OTHER PUBLICATIONS

H. Broxterman et al., Understanding the causes of multidrug resistance in cancer: a comparison of doxorubicin and sunitinib, Drug Resistance Updat. 12, 114-126. 2009.

M. Isaac et al., The oncogenic PIM kinase family regulates drug resistance through multiple mechanisms, Drug Resistance Updates, 14, 203- 211, 2011.

S. Mumenthaler et al., Pharmacologic inhibition of Pim kinases alters prostate cancer cell growth and resensitizes chemoresistant cells to taxanes, Mol. Cancer Ther. 8, 2882-2893, 2009.

L. Jackson et al., The role of PIM kinases in human and mouse CD4+ T cell activation and inflammatory bowel disease, Cellular Immunology, 272, 200-213, 2012.

* cited by examiner

PYRIMIDINE DERIVATIVES AS PIM KINASE INHIBITORS AND PREPARATION METHODS AND USE IN MEDICINAL MANUFACTURE THEREOF

CROSS-REFERENCE AND RELATED APPLICATIONS

The subject application is a continuation-in-part of U.S. patent application Ser. No. 14/177,156 filed on Feb. 10, 2014, now allowed, which is a continuation of PCT international application PCT/CN2012/001060 filed on Aug. 8, 2012, which in turn claims priority on Chinese patent applications CN 201110229731.X filed on Aug. 11, 2011 and CN 201210271738.2 filed on Aug. 1, 2012. The contents and subject matters of all the priority applications are incorporated herein by reference.

TECHNICAL FIELD

The present invention relates to medicinal chemistry, particularly, PIM kinase inhibitors, methods of preparation, and their pharmaceutical application in treating diseases.

BACKGROUND

PIM kinase family consists of three homologous serine/threonine kinases, Pim-1, Pim-2, and Pim-3, which belongs to calmodulin-dependent protein kinase-related family (CAMK). Researchers have shown that PIM kinases are widely expressed in hematopoietic tissues (J. Biol. Chem., 280, 14168-14176, 2005; Blood, 105, 4477-4483, 2005) and play important roles in cell survival and proliferation. Since PIM kinases are overexpressed in a variety of malignancies and inflammations (J. Exp. Med., 201, 259-266, 2005; Biochem. Soc. Trans., 32, 315-319, 2004), they are more and more being targeted for treating cancers and immune dysfunctions. PIM-1 (Provirus Integration of Maloney 1) is originally identified in a series of insertional mutagenesis studies of retroviruses, as a frequent proviral integration site in Moloney murine leukemia virus-induced T-cell lymphomas, and PIM-1 is named based on that finding (Cell, 37, 141-150, 1984). It is found later that the genes encoding PIM-2 (Provirus Integration of Maloney 2) have the same defect (J. Clin. Invest., 115, 2679-2688, 2005). Pim-2 has similar effects as and compensatory to Pim-1 (J EMBO, 14, 2536, 1995). PIM-3 is initially named as KID-1 (Kinase Induced by Depolarization 1), but renamed to Pim-3 because of its high sequence similarity to Pim-1 (Nature, 428, 332-337, 2005; Cell, 56, 673-682, 1989). PIM-1, 2, 3 are overly expressed in many hematopoietic malignancies (Proc. Natl. Acad. Sci. U.S.A., 86, 8857-8861, 1989). PIM-1 is found to be overexpressed in the development of prostate cancer (J. Clin. Pathol., 59, 285-288, 2006). PIM-2 expression is elevated in human chronic lymphocytic leukemia and non-Hodgkin's lymphoma leukemia (Leuk. Lymph., 45, 951-955, 2004), the aberrant expression of PIM-3 is believed to have played an important role in the development and proliferation of liver fibroma (Int. J. Cancer, 114, 209-218, 2005) and pancreatic cancer (Cancer Res., 66, 6741-6747, 2006).

PIM-1, PIM-2, and PIM-3 have effects on the survival and proliferation of hematopoietic cells in response to growth factors stimulation. PIM-1, 2, 3 triple knockout mice are viable and fertile while displaying reduced body size and impairment of proliferation of hematopoietic cells in response to growth factors. Knocking out one of 3 kinases does not have obvious effect on mice, indicating some overlapping functions among PIM kinases (Cell, 56, 673-682, 1989). The substrates of PIM kinases include Bcl-2 family members such as pro-apoptotic BAD protein (FEBS Letters, 571, 43-49, 2004), cell cycle regulating p21 (Biochem. Biophys. Acta, 1593, 45-55, 2002), CDC25A, C-TA (J. Biol. Chem., 279, 48319-48328, 2004), protein synthesis related 4EBP1 (Blood, 105, 4477-4483, 2005). These functions of PIM kinases indicate that PIM kinases can prevent apoptosis and promote cell growth and proliferation. Their overexpression in cancer cells promotes the survival and proliferation of the cancer cells. Therefore, inhibiting the PIM kinase activities in cancer cell is a new effective way of treating cancers.

Based on the evidence that PIM kinases are involved in hematological cancers and solid tumors, a number of PIM inhibitors have been developed to treat a variety of cancers. It is shown in a series of cellular assays and in vivo models that PIM inhibitors can significantly inhibit Acute Lymphoblastic Leukemia (ALL), Acute Myeloid Leukemia (AML), Chronic myelogenous leukemia (CML), Non-Hodgkin's Lymphoma (NHL), and Multiple Myeloma (MM) cell proliferation and tumor growth in xenograft model (Clin. Cancer Res. 20(7), 1834-1845, 2014; Blood 123(6), 905-913, 2014; Blood 122(21), 4435, 2013). It has also been demonstrated that PIM inhibitors are useful to treat PIM overexpressed solid tumors such as pancreatic cancers (Cancer Biol. Ther. 7(9), 1352-9, 2008 Cancer Res. 2006; 66(13): 6741-7; Cancer Res. 70(24), 10288-10298, 2010), prostate cancers (Prostate, 65(3), 276-86, 2005; Prostate, 73(13), 1462-1469, 2013), liver cancers (J. Surg. Res., 153(1), 17-22, 2009; Int. J. Cancer, 114(2), 209-18, 2005), gastric cancer (J. Cancer Res. Clin. Oncol., 134(4), 481-8, 2008), and bladder cancer (J. Exp. Clin. Cancer Res., 29, 161, 2010).

Moreover, resistance to chemotherapeutics and molecularly targeted drugs is a major obstacle in cancer treatment (Drug Resistance Updat. 12, 114-126. 2009). It has also been reported that PIM kinases are involved in the expression and activity of MDR-1 and BCRP, two of the most important drug efflux transporters. "It is abundantly clear from the preclinical models that PIM inhibition can significantly reverse drug resistant phenotypes." See Drug Resistance Updates, 14, 203-211, 2011. It has been demonstrated that the use of PIM inhibitors in combination with chemotherapeutics can significantly increase their potencies against drug resistant prostate cancer (Mol. Cancer Ther. 8, 2882-2893, 2009). Therefore, PIM kinase inhibitors are used to reverse the multi drug resistance.

Further, PIM kinases are expressed following T cell activation. Studies show that therapeutic dosing of a PIM-1/3 inhibitor is efficacious in a CD4+ T cell-mediated model of inflammatory bowel disease. Oral administration of AR452530 significantly decreases colon inflammation, gland loss, edema, and mucosal thickness by at least 80%. Therefore, PIM-1/3 kinases have an important role in CD4+ T cell responses and inhibition of this activity may provide a therapeutic benefit in T cell-mediated diseases. See Cellular Immunology, 272, 200-213, 2012.

SUMMARY OF THE INVENTION

The present invention provides chemical compounds having certain biological activities that include, but not limited to, inhibiting cell proliferation, promoting apoptosis, and modulating protein kinase activities. The present invention provides compounds that inhibit the activities of PIM-1, PIM-2 and PIM-3 kinases. The present invention also provides methods for preparing the novel chemical compounds and analogs thereof, and methods of using these compounds to treat cancers, autoimmune diseases, allergic reactions, and organ transplant rejection.

The PIM kinase inhibitors of the present invention have the following general structural Formula I, and their stereoisomers, tautomers, and pharmaceutically acceptable salts,

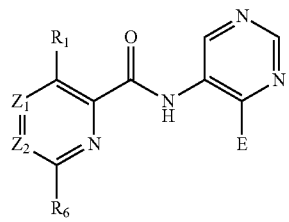

I wherein $Z_1$ and $Z_2$ are independently selected from a $CR_2$, a $CR_3$, and a nitrogen (N), provided that $Z_1$ and $Z_2$ cannot be N at the same time;

$R_1$ is a hydrogen (H), —$NHR_4$, a halogen, a hydroxyl, an alkyl, a cyano, or a nitro group;

$R_2$ and $R_3$ are each independently selected from a hydrogen, —$NHR_5$, a halogen, a hydroxyl, a substituted or unsubstituted alkyl, an alkenyl, an alkynyl, an alkoxyl, a cycloalkyl, an amino, a cyano, and a nitro group;

$R_4$ is a hydrogen, —C(=O)—$R_5$, a substituted or unsubstituted alkyl, a cycloalkyl, a heterocyclyl, an aryl, or a heteroaryl;

$R_5$ is a substituted or unsubstituted alkyl, an alkenyl, an alkynyl, an alkoxyl, a cycloalkyl, an amino, or a substituted amino group;

$R_6$ is a substituted or unsubstituted aryl, a heteroaryl, a cycloalkyl, where each substituted $R_6$ group is substituted with up to four substituents that is a halogen, a cyano, an amino, a $C_{1-4}$ alkyl, a $C_{3-6}$ cycloalkyl, an alkoxyl, a nitro, a carboxy, a carbonyl, a carboalkoxy, or an aminocarboxy;

E is an $OR_{22}$, a $SR_{22}$, or a $SO_2R_{22}$; $R_{22}$ is an optionally substituted $C_1$-$C_8$ hydrocarbon group or a group described in the following formula:

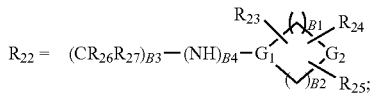

wherein each of $R_{23}$, $R_{24}$, $R_{25}$ is independently selected from a H, a halogen, an $OR_{15}$, a $NR_{16}R_{17}$, a C(=O)N$R_{18}R_{19}$, or an optionally substituted $C_1$-$C_8$ hydrocarbon group; or $R_{23}$, $R_{24}$ and $R_{25}$, together with the atoms to which they are attached, may be joined together to form a chain so that the ring to which they are attached is a substituted $C_6$-$C_{14}$ membered spiral ring, a bicyclic ring, or a fused ring group;

$G_1$ is —CH or N;
$G_2$ is $NR_{28}$, $CHR_{29}$ or O;
B1 and B2 each independently represents 0, 1, 2, or 3;
B3 is 0, 1, or 2;
B4 is 0 or 1;

Each of $R_{16}$, $R_{17}$, $R_{18}$, $R_{19}$, $R_{26}$ and $R_{27}$ is independently selected from a H or an optionally substituted $C_1$-$C_8$ hydrocarbon group;

$R_{28}$ is H, an optionally substituted hydrocarbon group, an optionally substituted cyclic hydrocarbon group, an optionally substituted heterocyclic hydrocarbon group, a C(=O)$R_{30}$, C(=O)O$R_{30}$, or a C(=O)NH$R_{30}$;

$R_{29}$ is an OH, a NH$R_{30}$, a C(=O)O$R_{30}$, or a C(=O)NH$R_{30}$; and $R_{30}$ is H or an optionally substituted $C_1$-$C_8$ hydrocarbon group.

In some embodiments of the present invention, the compounds of Formula I or a stereoisomer, tautomer, or pharmaceutically acceptable salt thereof have $Z_1$ and $Z_2$ that are $CR_2$ and $CR_3$, respectively.

In some other embodiments of the present invention, the compounds of Formula I or a stereoisomer, tautomer, or pharmaceutically acceptable salt thereof have $R_2$ and $R_3$ that are independently selected from a hydrogen, a methyl, an ethyl, a halogen, and a cyano group.

In yet another embodiments of the present invention, in the compounds of Formula I and their stereoisomer, tautomer, or pharmaceutically acceptable salt thereof, $Z_1$ is $CR_2$, $Z_2$ is $CR_3$, and E is O—$R_{22}$, so that they have the following structure of formula II:

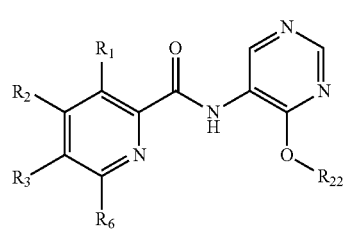

II

DETAILED DESCRIPTION OF THE INVENTION

The PIM kinase inhibitors of the present invention and their stereoisomers, tautomers, and pharmaceutically acceptable salts have the following general structural Formula I:

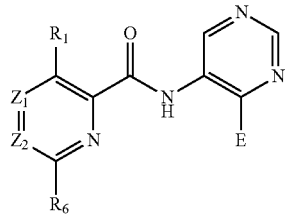

I wherein $Z_1$ and $Z_2$ are independently selected from a $CR_2$, a $CR_3$, and a nitrogen (N), provided that $Z_1$ and $Z_2$ cannot be N at the same time;

$R_1$ is a hydrogen (H), —$NHR_4$, a halogen, a hydroxyl, an alkyl, a cyano, or a nitro group;

$R_2$ and $R_3$ are each independently selected from a hydrogen, —$NHR_5$, a halogen, a hydroxyl, a substituted or unsubstituted alkyl, an alkenyl, an alkynyl, an alkoxyl, a cycloalkyl, an amino, a cyano, and a nitro group;

$R_4$ is a hydrogen, —C(=O)—$R_5$, a substituted or unsubstituted alkyl, a cycloalkyl, a heterocyclyl, an aryl, or a heteroaryl;

$R_5$ is a substituted or unsubstituted alkyl, an alkenyl, an alkynyl, an alkoxyl, a cycloalkyl, an amino, or a substituted amino group;

$R_6$ is a substituted or unsubstituted aryl, a heteroaryl, a cycloalkyl, where each substituted $R_6$ group may be substituted with up to four substituents that is a halogen, a cyano, an amino, a $C_{1-4}$ alkyl, a $C_{3-6}$ cycloalkyl, an alkoxyl, a nitro, a carboxy, a carbonyl, a carboalkoxy, or an aminocarboxy;

E is an $OR_{22}$, a $SR_{22}$, or a $SO_2R_{22}$; $R_{22}$ is an optionally substituted $C_1$-$C_8$ hydrocarbon group or a group described in the following formula:

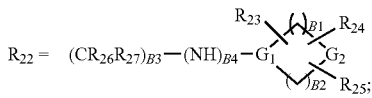

wherein each of $R_{23}$, $R_{24}$, $R_{25}$ is independently selected from a H, a halogen, an $OR_{15}$, a $NR_{16}R_{17}$, a $C(=O)NR_{18}R_{19}$, or an optionally substituted $C_1$-$C_8$ hydrocarbon group; or $R_{23}$, $R_{24}$ and $R_{25}$, together with the atoms to which they are attached, may be joined together to form a chain so that the ring to which they are attached is a substituted $C_6$-$C_{14}$ membered spiral ring, a bicyclic ring, or a fused ring group;

$G_1$ is —CH or N;
$G_2$ is $NR_{28}$, $CHR_{29}$ or O;
B1 and B2 each independently represents 0, 1, 2, or 3;
B3 is 0, 1, or 2;
B4 is 0 or 1;
Each of $R_{16}$, $R_{17}$, $R_{18}$, $R_{19}$, $R_{26}$ and $R_{27}$ is independently selected from a hydrogen (H) or an optionally substituted $C_1$-$C_8$ hydrocarbon group;

$R_{28}$ is H, an optionally substituted hydrocarbon group, an optionally substituted cyclic hydrocarbon group, an optionally substituted heterocyclic hydrocarbon group, a $C(=O)R_{30}$, $C(=O)OR_{30}$, or a $C(=O)NHR_{30}$;

$R_{29}$ is an OH, a $NHR_{30}$, a $C(=O)OR_{30}$, or a $C(=O)NHR_{30}$; and $R_{30}$ is H or an optionally substituted $C_1$-$C_8$ hydrocarbon group.

In some embodiments of the present invention, the compounds of Formula I or a stereoisomer, tautomer, or pharmaceutically acceptable salt thereof have $Z_1$ and $Z_2$ that are $CR_2$ and $CR_3$, respectively.

In some other embodiments of the present invention, the compounds of Formula I or a stereoisomer, tautomer, or pharmaceutically acceptable salt thereof have $R_2$ and $R_3$ that are independently selected from a hydrogen, a methyl, an ethyl, a halogen, and a cyano group.

In yet another embodiments of the present invention, the compounds of Formula I and their stereoisomer, tautomer, or pharmaceutically acceptable salt thereof have the structure of formula I where $Z_1$ is $CR_2$, $Z_2$ is $CR_3$, and E is O—$R_{22}$, and the structure is described as the following formula II:

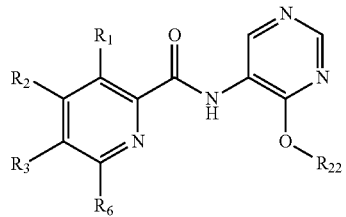

In some embodiments of the present invention, the compounds of Formula I or II, or a stereoisomer, tautomer, or pharmaceutically acceptable salt thereof are provided where $R_1$ is a hydrogen, an amino or a fluoro. Preferred embodiments of the compounds of Formula II of the present invention are provided at the following Table I.

In some embodiments of the present invention, the compounds of Formula I or II, or a stereoisomer, tautomer, or pharmaceutically acceptable salt thereof are provided where $R_6$ is a substituted or unsubstituted aryl, a hetero aryl, a $C_4$-$C_6$ cycloalkyl, a partially unsaturated $C_4$-$C_6$ cycloalkyl, where each group can be substituted with up to four substituents that is a halogen, a cyano, an amino, an alkyl, an alkoxy, a cycloalkyl, a nitro, a carboxyl, a carboalkoxy, an aminocarboxy, a substituted aminocarbonyl, an aminosulfonyl, a substituted aminosulfonyl, or an alkoxyalkyl.

In some embodiments of the present invention, the compounds of Formula I or II, or a stereoisomer, tautomer, or pharmaceutically acceptable salt thereof are provided where $R_6$ is a substituted or unsubstituted phenyl, where the phenyl group can be substituted with up to three substituents that is a hydrogen, a cyano, a nitro, a halogen, a hydroxyl, an amino, an alkoxy, a substituted amino, an alkyl, a cycloalkyl.

In some embodiments of the present invention, the compounds of Formula I or II or a stereoisomer, tautomer, or pharmaceutically acceptable salt thereof are provided where $R_6$ is 2,6-difluorophenyl.

In some embodiments of the present invention, the compounds of Formula I or II, or a stereoisomer, tautomer, or pharmaceutically acceptable salt thereof are provided where $R_2$ and $R_3$ are each independently selected from a hydrogen, a halogen, a cyano, a methyl, or an ethyl.

In some embodiments of the present invention, the compounds of Formula I or II, or a stereoisomer, tautomer, or pharmaceutically acceptable salt thereof are provided where $R_{22}$ is a substituted or unsubstituted cyclobutyl, a cyclopentyl, a cyclohexyl, a cycloheptyl, an azetidyl, a pyrrolidinyl, a piperidinyl, an azepanyl, an oxetyl, a tetrahydrofuryl, a tetrahydropyranyl, where the $R_{22}$ group may be substituted with up to three substitutents that is an amino, a hydroxy, a methyl, an ethyl, or a methoxy; $R_1$ is a hydrogen, an amino, or a fluoro; $R_2$ and $R_3$ are each independently selected from a hydrogen, a halogen, and a methyl; $R_6$ is a substituted or unsubstituted phenyl, where the phenyl group can be substituted with up to three substituents that is a hydrogen, a cyano, a nitro, a halogen, a hydroxyl, an amino, an alkoxy, a substituted amino, an alkyl, or a cycloalkyl.

In some embodiments of the present invention, the compounds of Formula I or II, or a stereoisomer, tautomer, or pharmaceutically acceptable salt thereof are provided where $R_{22}$ is a substituted or unsubstituted cyclobutylmethyl, a cyclopentylmethyl, a cyclohexylmethyl, a cycloheptylmethyl, an azetidylmethyl, a pyrrolidinylmethyl, a piperidinylmethyl, an azepanylmethyl, an oxetylmethyl, a tetrahydrofurylmethyl, a tetrahydropyranylmethyl, where the $R_{22}$ group may be substituted with up to three substitutents that is an amino, a hydroxy, a methyl, an ethyl, or a methoxy; $R_1$ is a hydrogen or an amino; $R_2$ and $R_3$ are each independently selected from a hydrogen, a halogen, and a methyl; $R_6$ is a substituted or unsubstituted phenyl, where the phenyl group can be substituted with up to three substituents that is a hydrogen, a cyano, a nitro, a halogen, a hydroxyl, an amino, an alkoxy, a substituted amino, an alkyl, or a cycloalkyl.

A preferred embodiment of the present inventions is a compound of Formula II, where $R_{22}$ is a substituted or unsubstituted cyclohexyl, azetidyl, pyrrolidinyl, piperidinyl, azepanyl, tetrahydrofuryl, or tetrahydropyranyl group, and preferably a cyclohexyl, pyrrolidinyl, piperidinyl, or azepanyl group, where the $R_{22}$ group may be substituted with up to three substitutents that is an amino, a hydroxy, a methyl, an ethyl, or a methoxy group, and preferably an amino, a hydroxy, or a methyl group; $R_1$ is a hydrogen, an amino, or a fluoro; $R_2$ and $R_3$ are each independently selected from a hydrogen, a halogen, and a methyl, and preferably $R_2$ is a hydrogen and $R_3$ is a halogen; $R_6$ is a substituted or unsubstituted phenyl, where the phenyl group can be substituted with up to three substituents that is a hydrogen, a cyano, a nitro, a halogen, a hydroxyl, an amino, an alkoxy, a substituted amino, an alkyl, or a cycloalkyl, and preferably a hydrogen, a cyano, or a halogen, and most preferably a hydrogen or a halogen.

Yet another preferred embodiment of the present inventions is a compound of Formula II, where $R_{22}$ is a substituted or unsubstituted cyclohexylmethyl, azetidylmethyl, pyrrolidinylmethyl, piperidinylmethyl, azepanylmethyl, tetrahydrofurylmethyl, or tetrahydropyranylmethyl group, and preferably, a cyclohexylmethyl, pyrrolidinylmethyl, piperidinylmethyl, or azepanylmethyl group, where the $R_{22}$ group may be substituted with up to three substituents that is an amino, hydroxy, methyl, ethyl, or methoxy, and preferable an amino, hydroxy, or methyl; $R_1$ is a hydrogen, an amino, or a fluoro; $R_2$ and $R_3$ are each independently selected from a hydrogen, a halogen, and methyl, and preferably $R_2$ is a hydrogen and $R_3$ is a halogen; $R_6$ is a substituted or unsubstituted phenyl, where the phenyl group can be substituted with up to three substituents that is a hydrogen, a cyano, a nitro, halogen, hydroxyl, an amino, an alkoxy, a substituted amino, an alkyl, or a cycloalkyl, and preferably a hydrogen, a cyano, or a halogen, and most preferably a hydrogen or a halogen.

Yet another preferred embodiment of the present inventions is a compound of Formula II, wherein $R_{22}$ is a substituted $C_2$-$C_5$ alkyl, the substituted $R_{22}$ group may be substituted at any position on the substituent with up to four substitutents that is an amino, an alkylamino, a hydroxy, a halogen, a methyl, an ethyl, a halogenated methyl, or a halogenated ethyl group; $R_1$ is a hydrogen, an amino, or a fluoro; $R_2$ is a hydrogen; $R_3$ is, a halol; and $R_6$ is a substituted or unsubstituted phenyl, and the substituted phenyl group is substituted with up to three substituents that is a hydrogen, a methyl, or a halogen.

As used herein, the term 'substituent' refers to atom or atomic group that replaces the hydrogen atoms of the molecule. As used herein, 'optionally substituted' substituent refers to substituents that each of the replicable hydrogen atoms on the substituents may be substituted by other atom or atomic group.

As used herein, the term 'hydrocarbon group' refers to alkyl group (saturated aliphatic group), alkenyl group (having at least one carbon-carbon double bond), alkynyl group (having at least one carbon-carbon triple bond); the 'hydrocarbon group' may be linear, branched or cyclic; the 'hydrocarbon group' may be aliphatic or aromatic.

As used herein, the term 'cyclic hydrocarbon group' refers to cycloalkyl group or cycloalkenyl group (having at least one carbon-carbon double bond), aromatic group; 'cyclic hydrocarbon group' may be monocyclic, bicyclic or multi-cyclic group; 'cyclic hydrocarbon group' may be spiral or fused ring.

As used herein, the term 'hetero cyclic hydrocarbon group' refers to cycloalkyl group or cycloalkenyl group (having at least one carbon-carbon double bond), aromatic group with one or more ring atoms are hetero atoms such as N, O, S, or combination thereof; 'hetero cyclic hydrocarbon group' may be monocyclic, bicyclic or multi-cyclic group; 'hetero cyclic hydrocarbon group' may be spiral or fused ring.

As used herein, the term 'substituent' include but not limited to: halogen (F, Cl, Br, I), —$OR_{26}$, —OC(=O) $R_{26}$, —OC(=O)N $R_{26}R_{27}$, =O, —$SR_{26}$, —$SOR_{26}$, —$SO_2R_{26}$, —$SO_2N$ $R_{26}R_{27}$, —C(=O)$R_{26}$, —C(=O)$OR_{26}$, —C(=O)N $R_{26}R_{27}$, —$R_{26}$CN, —$NR_{26}R_{27}$, —NHC(=O) $R_{26}$, —NHC(=O)N $R_{26}R_{27}$, —NHC(=S)N $R_{26}R_{27}$, halogenated (F, Cl, Br, I) hydrocarbon; and each of $R_{26}$ and $R_{27}$ is independently selected from H or optionally substituted $C_1$-$C_8$ hydrocarbon group.

The compounds described in the present invention that are acidic in nature can form pharmaceutically acceptable salts by reacting with physiologically compatible organic or inorganic bases, such as readily soluble alkali and alkaline earth salts, and salts formed from reacting with ammonia, N-methyl-glucamine, dimethyl-glucamine, ethyl-glucamine, lysine, ethanolamine, glucosamine, sarcosine, serine, tris(hydroxymethyl)aminomethane, 1-amino-2,3,4-butanetriol.

The compounds described in the present invention that are basic in nature can form pharmaceutically acceptable salts by reacting with physiologically compatible organic or inorganic acids, such as the salts formed by reacting with hydrochloric acid, hydrobromic acid, sulfuric acid, phosphoric acid, methanesulfonic acid, toluene-sulfonic acid, carbonic acid, succinic acid, citric acid, benzoic acid, oxalic acid, malonic acid, salicylic acid, malic acid, fumaric acid, maleic acid, acetic acid, ascorbic acid.

The compounds in the present invention may be pure chiral compounds, racemic mixtures, optically active compounds, pure diastereomers, or mixed diastereomers.

The present invention provides PIM kinase inhibitors which include the following compounds:
6-(2,6-difluorophenyl)-5-fluoro-N-(4-(piperidin-4-ylmethoxy)pyrimidin-5-yl)picolinamide, N-(4-(azetidin-3-ylmethoxy)pyrimidin-5-yl)-6-(2,6-difluorophenyl)-5-fluoropicolinamide, 6-(2,6-difluorophenyl)-5-fluoro-N-(4-(piperidin-4-yloxy)pyrimidin-5-yl)picolinamide, 6-(2,6-difluorophenyl)-5-fluoro-N-(4-(pyrrolidin-3-yloxy) pyrimidin-5-yl)picolinamide, 6-(2,6-difluorophenyl)-5-fluoro-N-(4-(piperidin-3-yloxy)pyrimidin-5-yl) picolinamide, N-(4-(azocan-4-yloxy)pyrimidin-5-yl)-6-(2,6-difluorophenyl)-5-fluoropicolinamide, 6-(2,6-difluorophenyl)-5-fluoro-N-(4-(piperidin-3-ylmethoxy) pyrimidin-5-yl)picolinamide, 6-(2,6-difluorophenyl)-5-fluoro-N-(4-(pyrrolidin-3-ylmethoxy)pyrimidin-5-yl) picolinamide, N-(4-(azetidin-3-yloxy)pyrimidin-5-yl)-6-(2, 6-difluorophenyl)-5-fluoropicolinamide, N-(4-(((1r,4r)-4-aminocyclohexyl)oxy)pyrimidin-5-yl)-6-(2,6-difluorophenyl)-5-fluoropicolinamide, N-(4-((3-aminocyclohexyl)oxy)pyrimidin-5-yl)-6-(2,6-difluorophenyl)-5-fluoropicolinamide, N-(4-(3-aminopropoxyl)pyrimidin-5-yl)-6-(2,6-difluorophenyl)-5-fluoropicolinamide, 6-(2,6-difluorophenyl)-5-fluoro-N-(4-(3-(methylamino)propoxy)pyrimidin-5-yl)picolinamide, 6-(2,6-difluorophenyl)-N-(4-(3-(dimethylamino)propoxy) pyrimidin-5-yl)-5-fluoropicolinamide, N-(4-(4-aminobutoxyl)pyrimidin-5-yl)-6-(2,6-difluorophenyl)-5-fluoropicolinamide, 6-(2,6-difluorophenyl)-5-fluoro-N-(4-(4-(methylamino)butoxy)pyrimidin-5-yl)picolinamide, 6-(2,6-difluorophenyl)-5-fluoro-N-(4-(3-hydroxypropoxyl) pyrimidin-5-yl)picolinamide, 6-(2,6-difluorophenyl)-5-fluoro-N-(4-(3-hydroxybutoxyl)pyrimidin-5-yl) picolinamide, 6-(2,6-difluorophenyl)-5-fluoro-N-(4-(4-hydroxybutoxyl)pyrimidin-5-yl)picolinamide, 6-(2,6- difluorophenyl)-5-fluoro-N-(4-((4-hydroxy-4-methylpentyl)oxy) pyrimidin-5-yl)picolinamide, 6-(2,6-difluorophenyl)-N-(4-(3,4-dihydroxybutoxyl)pyrimidin-5-yl)-5-fluoropicolinamide, N-(4-(3-amino-4-hydroxybutoxy)pyrimidin-5-yl)-6-(2,6-difluorophenyl)-5-fluoropicolinamide, 6-(2,6-difluorophenyl)-5-fluoro-N-(4-((tetrahydro-2H-pyran-4-yl)methoxy)pyrimidin-5-yl)picolinamide, 3-amino-6-(2,6-difluorophenyl)-5-fluoro-N-(4-(piperidin-4-ylmethoxy)pyrimidin-5-yl)picolinamide, 3-amino-6-(2,6-difluorophenyl)-5-fluoro-N-(4-(pyrrolidin-3-yloxy)pyrimidin-5-yl)picolinamide, 3-amino-6-(2,6-difluorophenyl)-5-fluoro-N-(4-(piperidin-4-yloxy)pyrimidin-5-yl)picolinamide, 3-amino-N-(4-(azepan-4-yloxy)pyrimidin-5-yl)-6-(2,6-difluorophenyl)-5-fluoropicolinamide, 3-amino-N-(4-(((1r,4r)-4-aminocyclohexyl)oxy)pyrimidin-5-yl)-6-(2,6-difluorophenyl)-5-fluoropicolinamide, 3-amino-6-(2,6-difluorophenyl)-5-fluoro-N-(4-(pyrrolidin-3-ylmethoxy)pyrimidin-5-yl)picolinamideyl)picolinamide, N-(4-((1-amino-3-chloropropan-2-yl)oxy)pyrimidin-5-yl)-6-(2,6-difluorophenyl)-5-fluoropicolinamide, N-(4-(3-amino-2-(chloromethyl)propoxy)pyrimidin-5-yl)-6-(2,6-difluorophenyl)-5-fluoropicolinamide.

The present invention also provides the methods of synthesis of the above PIM kinase inhibitors. The compounds in the present invention are made from commercially available starting materials and reagents. The present invention is illustrated in the following reaction scheme:

(1) The general procedure for the synthesis of compounds of Formula II:

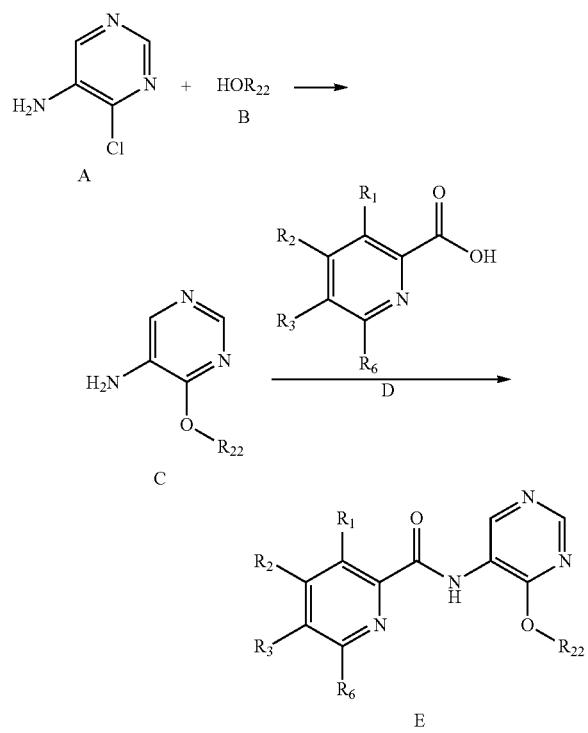

Alcohol B (1.1 eq.), protected or unprotected, reacts with a base, for example, NaH (1.1 eq.), in a solvent, for example, THF, at room temperature (25° C.) for 1 hour, then reacts with 5-amino-4-chloropyrimidine A (1 eq.) at heated conditions, for example, 100° C. for 1-10 hours to form aminopyrimidine ether C. Protected or unprotected aromatic carboxylic acid D (1 eq.), in the presence of a coupling reagent, for example, HATU (1-1.5 eq.), a base, for example, DIEA (3 eq.), in a solvent, for example DMF, at heated conditions, for example 40° C., reacts with amine C (1 eq.) for 0.5-8 hours to form ether E. If there is no protecting group in E, then E is final ether product of Formula I or II. If E is protected by protecting group, for example, BOC or trimethylsilyl group, it's deprotected by treating with trifluoroacetic acid (10-100 eq.) with equal volume of dichloromethane at room temperature (25° C.) for 1-16 hours. The final ether product F of Formula I or II is obtained after removing the solvent in vacuo at room temperature (25° C.).

The present invention also provides the pharmaceutical application of the above PIM kinase inhibitors.

The PIM kinase assays show that all compounds in all the examples can significantly inhibit the PIM-1, PIM-2 and PIM-3 activity. The $IC_{50}$ of these compounds range from 0.1 nM to 50 nM. Therefore, the PIM kinase inhibitors in the present invention may be used for pharmaceuticals.

The present invention provides the use of the above PIM kinase inhibitors as drugs to treat or prevent hematological cancers such as human chronic lymphocytic leukemia, Acute Lymphoblastic Leukemia (ALL), Acute Myeloid Leukemia (AML), Chronic myelogenous leukemia (CML), Non-Hodgkin's Lymphoma (NHL) and Multiple Myeloma (MM) and solid tumors such as pancreatic cancers, prostate cancers, liver cancers, gastric cancer and bladder cancer, and the PIM kinase inhibitors of the present invention further may be used to treat or prevent multi drug resistance, and T cell-mediated diseases such Inflammatory Bowel Disease (IBD). The present invention further provides the use of the PIM kinase inhibitors of the present invention as drugs to treat or prevent autoimmune diseases.

The drugs in present invention use PIM kinase inhibitors as active ingredients along with pharmaceutical carriers and adjuvants. The present invention provides the new application of PIM kinase inhibitors and has significant clinical value.

EXAMPLES

The following examples are set forth for illustration only to help understand the invention described herein and not to be construed as limiting the present invention in any manner.

Example 1

Synthesis of 6-(2,6-difluorophenyl)-5-fluoro-N-(4-(piperidin-4-ylmethoxy)pyrimidin-5-yl)picolinamide (1)

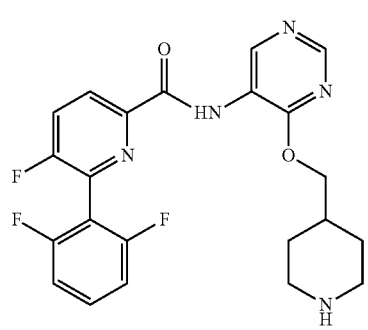

(1) tert-butyl 4-(((5-aminopyrimidin-4-yl)oxy)methyl)piperidine-1-carboxylate (C1)

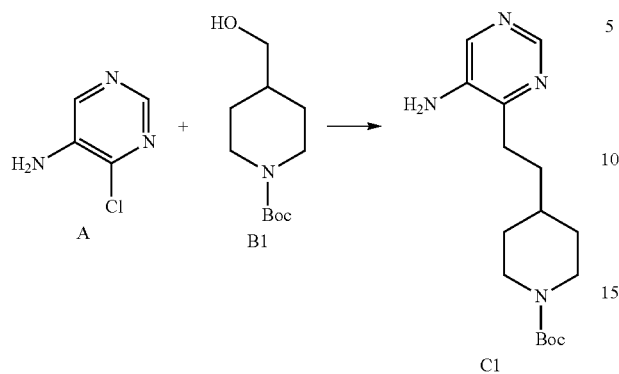

At room temperature, NaH (67 mg, 2.79 mmol) was added to a solution of tert-butyl 4-(hydroxymethyl)piperidine-1-carboxylate (B1) (500 mg, 2.32 mmol) in THF (tetrahydrofuran) (10 mL) and stirred for 1 hour. 4-chloropyrimidin-5-amine (A) (346 mg, 2.67 mmol) was then added. The reaction mixture was then heated to 100° C. under nitrogen and stirred for 4 hours, cooled to room temperature (20-30° C.) and concentrated in vacuo. The residue was purified with flash column (eluent: 10-30% ethyl acetate/petroleum ether) to obtain the product C1 (370 mg, 1.2 mmol).

(2) Synthesis of tert-butyl 4-4(5-(6-(2,6-difluorophenyl)-5-fluoropicolinamido)pyrimidin-4-yl)oxy)methyl)piperidine-1-carboxylate (E1)

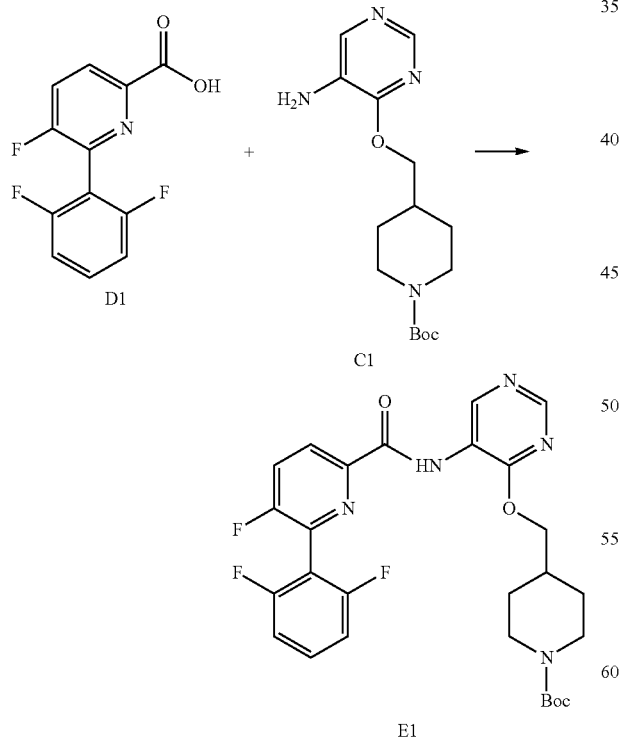

Compound (C1) (49 mg, 0.16 mmol), 6-(2,6-difluorophenyl)-5-fluoropicolinic acid (D1) (40 mg, 0.16 mmol, HATU (72 mg, 0.19 mmol) and DIEA (88 μL, 0.507 mmol) are mixed in DMF (5 mL) and stirred at 50° C. for 1 hour. The reaction mixture was cooled to room temperature and diluted with ethyl acetate (50 mL), washed with brine, dried over Na$_2$SO$_4$, and concentrated in vacuo. The residue was purified with flash column (eluent: 10-30% ethyl acetate/petroleum ether) to obtain the product E1 (30 mg, 0.055 mmol).

(3) Synthesis of 6-(2,6-difluorophenyl)-5-fluoro-N-(4-(piperidin-4-ylmethoxy)pyrimidin-5-yl)picolinamide (1)

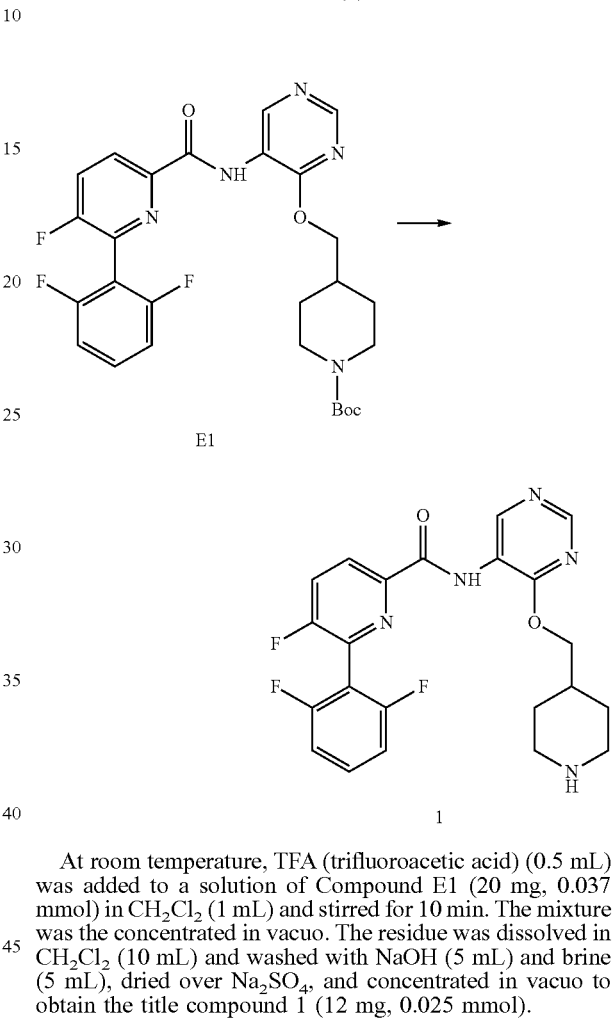

At room temperature, TFA (trifluoroacetic acid) (0.5 mL) was added to a solution of Compound E1 (20 mg, 0.037 mmol) in CH$_2$Cl$_2$ (1 mL) and stirred for 10 min. The mixture was the concentrated in vacuo. The residue was dissolved in CH$_2$Cl$_2$ (10 mL) and washed with NaOH (5 mL) and brine (5 mL), dried over Na$_2$SO$_4$, and concentrated in vacuo to obtain the title compound 1 (12 mg, 0.025 mmol).

Example 2

Synthesis of N-(4-(azetidin-3-ylmethoxy)pyrimidin-5-yl)-6-(2,6-difluorophenyl)-5-fluoropicolinamide (2)

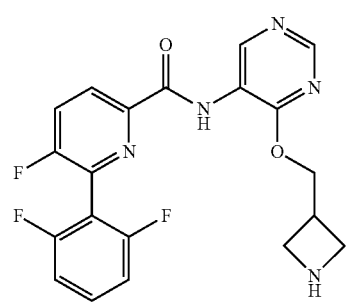

Following the procedure described in Example 1, and substituting compound B1 in Step (1) with tert-butyl 3-(hydroxymethyl)azetidine-1-carboxylate (B2), the title compound 2 was obtained.

Example 3

Synthesis of 6-(2,6-difluorophenyl)-5-fluoro-N-(4-(piperidin-4-yloxy)pyrimidin-5-yl)picolinamide (3)

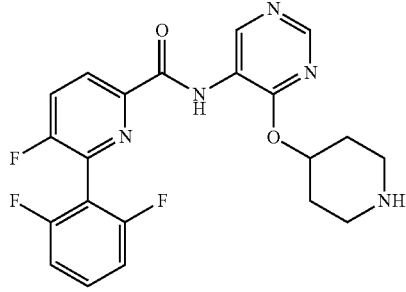

3

Following the procedure described in Example 1, and substituting compound B1 in Step (1) with tert-butyl 4-hydroxypiperidine-1-carboxylate (B3), the title compound 3 was obtained.

Example 4

Synthesis of 6-(2,6-difluorophenyl)-5-fluoro-N-(4-(pyrrolidin-3-yloxy)pyrimidin-5-yl)picolinamide (4)

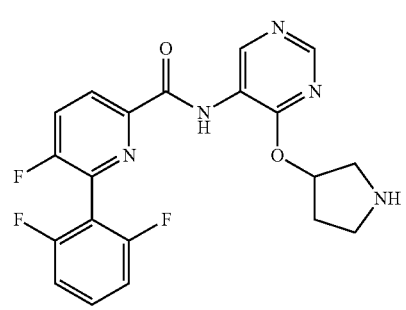

4

Following the procedure described in Example 1, and substituting Compound B1 in Step (1) with tert-butyl 3-hydroxypyrrolidine-1-carboxylate (B4), the title compound 4 was obtained.

Example 5

Synthesis of 6-(2,6-difluorophenyl)-5-fluoro-N-(4-(piperidin-3-yloxy)pyrimidin-5-yl)picolinamide (5)

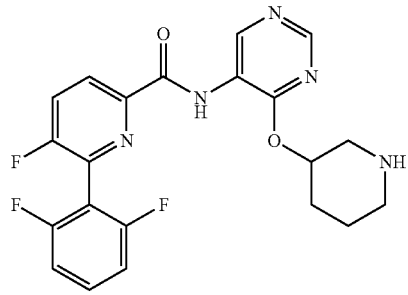

5

Following the procedure described in Example 1, and substituting Compound B1 in Step (1) with tert-butyl 3-hydroxypiperidine-1-carboxylate (B5), the title compound 5 was obtained.

Example 6

Synthesis of N-(4-(azepan-4-yloxy)pyrimidin-5-yl)-6-(2,6-difluorophenyl)-5-fluoropicolinamide (6)

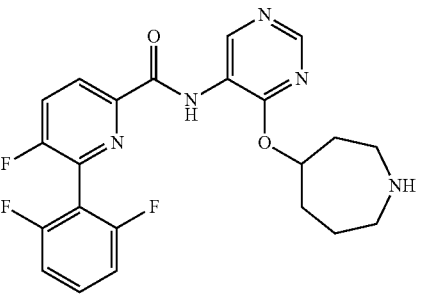

6

Following the procedure described in Example 1, and substituting Compound B1 in Step (1) with tert-butyl 4-hydroxyazepane-1-carboxylate (B6), the title compound 6 was obtained.

Example 7

Synthesis of 6-(2,6-difluorophenyl)-5-fluoro-N-(4-(piperidin-3-ylmethoxy)pyrimidin-5-yl)picolinamide (7)

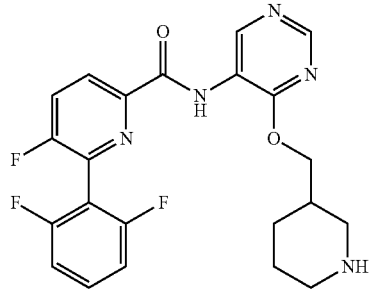

7

Following the procedure described in Example 1, and substituting Compound B1 in Step (1) with tert-butyl 3-(hydroxymethyl)piperidine-1-carboxylate (B7), the title compound 7 was obtained.

Example 8

Synthesis of 6-(2,6-difluorophenyl)-5-fluoro-N-(4-(pyrrolidin-3-ylmethoxy)pyrimidin-5-yl)picolinamide (8)

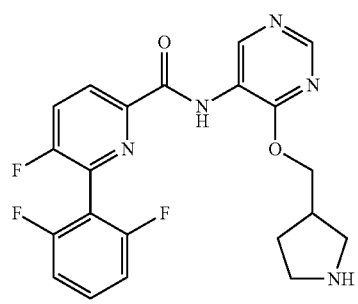

8

Following the procedure described in Example 1, and substituting Compound B1 in Step (1) with tert-butyl 3-(hydroxymethyl)pyrrolidine-1-carboxylate (B8), the title compound 8 was obtained.

Example 9

Synthesis of N-(4-(azetidin-3-yloxy)pyrimidin-5-yl)-6-(2,6-difluorophenyl)-5-fluoropicolinamide (9)

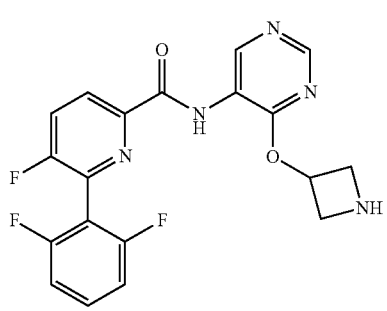

9

Following the procedure described in Example 1, and substituting Compound B1 in Step (1) with tert-butyl 3-(hydroxymethyl)azetidine-1-carboxylate (B9), the title compound 9 was obtained.

Example 10

Synthesis of N-(4-(((1r,4r)-4-aminocyclohexyl)oxy)pyrimidin-5-yl)-6-(2,6-difluorophenyl)-5-fluoropicolinamide (10)

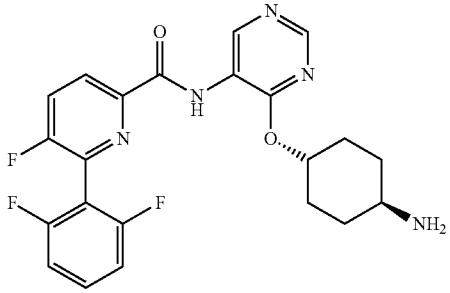

10

Following the procedure described in Example 1, and substituting Compound B1 in Step (1) with tert-butyl ((1r,4r)-4-hydroxycyclohexyl)carbamate (B10), the title compound 10 was obtained.

Example 11

Synthesis of N-(4-((3-aminocyclohexyl)oxy)pyrimidin-5-yl)-6-(2,6-difluorophenyl)-5-fluoropicolinamide (11)

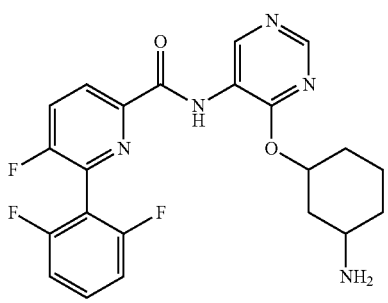

11

Following the procedure described in Example 1, and substituting Compound 1E in Step (1) with tert-butyl(3-hydroxycyclohexyl)carbamate (B11), the title compound 11 was obtained.

Example 12

Synthesis of N-(4-(3-aminopropoxyl)pyrimidin-5-yl)-6-(2,6-difluorophenyl)-5-fluoropicolinamide (12)

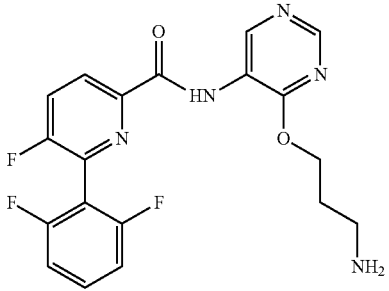

12

Following the procedure described in Example 1, and substituting Compound B1 in Step (1) with tert-butyl(3-hydroxypropyl)carbamate (B12), the title compound 12 was obtained.

Example 13

Synthesis of 6-(2,6-difluorophenyl)-5-fluoro-N-(4-(3-(methylamino)propoxy)pyrimidin-5-yl)picolinamide (13)

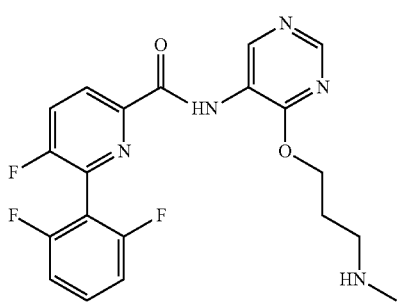

Following the procedure described in Example 1, and substituting Compound B1 in Step (1) with 3-(methylamino)propan-1-ol (B13), the title compound 13 was obtained.

Example 14

Synthesis of 6-(2,6-difluorophenyl)-N-(4-(3-(dimethylamino)propoxy)pyrimidin-5-yl)-5-fluoropicolinamide (14)

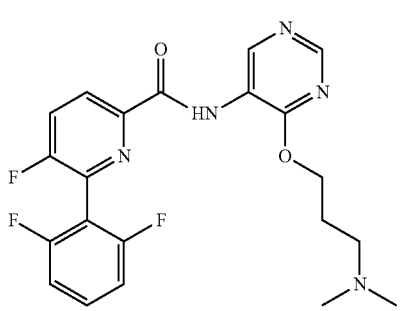

Following the procedure described in Example 1, and substituting Compound B1 in Step (1) with 3-(dimethylamino)propan-1-ol (B14), the title compound 14 was obtained.

Example 15

Synthesis of N-(4-(4-aminobutoxyl)pyrimidin-5-yl)-6-(2,6-difluorophenyl)-5-fluoropicolinamide (15)

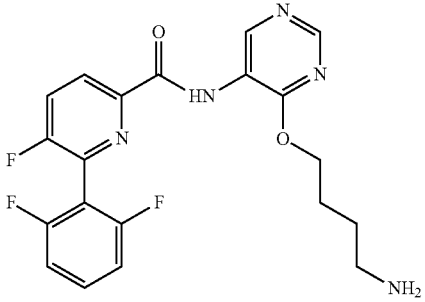

Following the procedure described in Example 1, and substituting Compound B1 in Step (1) with tert-butyl(4-hydroxybutyl)carbamate (B15), the title compound 15 was obtained.

Example 16

Synthesis of 6-(2,6-difluorophenyl)-5-fluoro-N-(4-(4-(methylamino)butoxy)pyrimidin-5-yl)picolinamide (16)

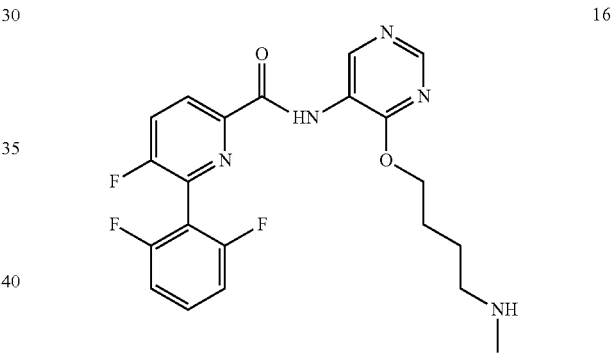

Following the procedure described in Example 1, and substituting Compound B1 in Step (1) with tert-butyl(4-hydroxybutyl)(methyl)carbamate (B16), the title compound 16 was obtained.

Example 17

Synthesis of 6-(2,6-difluorophenyl)-5-fluoro-N-(4-(3-hydroxypropoxyl)pyrimidin-5-yl)picolinamide (17)

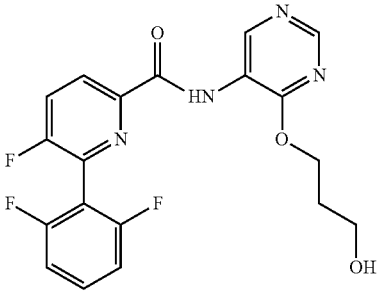

Following the procedure described in Example 1, and substituting Compound B1 in Step (1) with propane-1,3-diol (B17), the title compound 17 was obtained.

Example 18

Synthesis of 6-(2,6-difluorophenyl)-5-fluoro-N-(4-(3-hydroxybutoxyl)pyrimidin-5-yl)picolinamide (18)

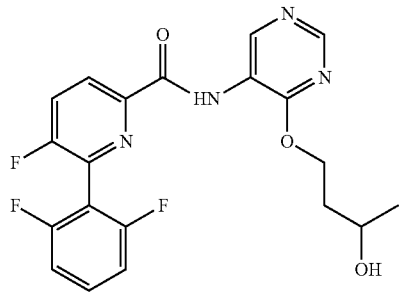

Following the procedure described in Example 1, and substituting Compound B1 in Step (1) with butane-1,3-diol (B18), the title compound 18 was obtained.

Example 19

Synthesis of 6-(2,6-difluorophenyl)-5-fluoro-N-(4-(4-hydroxybutoxyl)pyrimidin-5-yl)picolinamide (19)

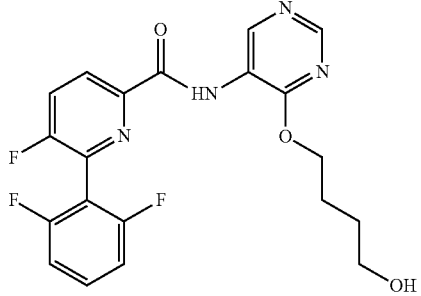

Following the procedure described in Example 1, and substituting Compound B1 in Step (1) with butane-1,4-diol (B4), the title compound 19 was obtained.

Example 20

Synthesis of 6-(2,6-difluorophenyl)-5-fluoro-N-(4-((4-hydroxy-4-methylpentyl)oxy)pyrimidin-5-yl)picolinamide (20)

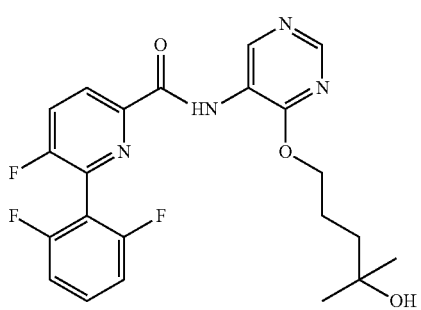

Following the procedure described in Example 1, and substituting Compound B1 in Step (1) with 4-methylpentane-1,4-diol (20), the title compound 20 was obtained.

Example 21

Synthesis of 6-(2,6-difluorophenyl)-N-(4-(3,4-dihydroxybutoxyl)pyrimidin-5-yl)-5-fluoropicolinamide (21)

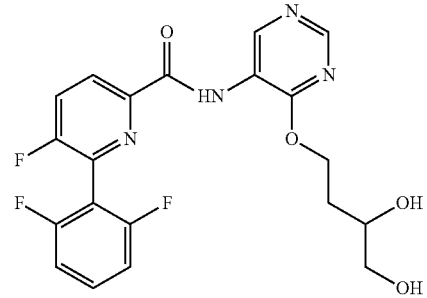

(1) The synthesis of 6-(2,6-difluorophenyl)-N-(4-(2-(2,2-dimethyl-1,3-dioxolan-4-yl)ethoxy)pyrimidin-5-yl)-5-fluoropicolinamide (E21)

Following the procedure described in Example 1, Step (1) and (2), and substituting Compound B1 in Step (1) with 2-(2,2-dimethyl-1,3-dioxolan-4-yl)ethanol (B21), compound E21 was obtained.

(2) 6-(2,6-difluorophenyl)-N-(4-(3,4-dihydroxybutoxyl)pyrimidin-5-yl)-5-fluoropicolinamide (21)

-continued

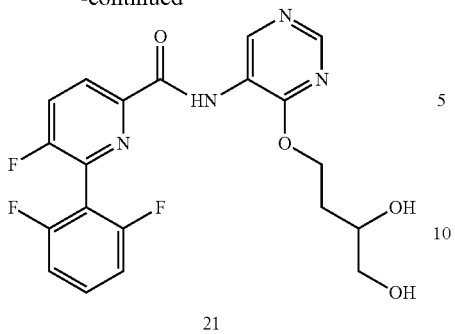

21

At room temperature (25° C.), to a solution of 6-(2,6-difluorophenyl)-N-(4-(2-(2,2-dimethyl-1,3-dioxolan-4-yl)ethoxy)pyrimidin-5-yl)-5-fluoropicolinamide (E21) (20 mg, 0.042 mmol) in methanol (2 mL) was added concentrated HCl (0.5 mL) and the solution was stirred for 4 hours. 10% Na$_2$CO$_3$ solution was added to neutralize the solution to pH=7, the water (20 mL) was added and a precipitate was formed. An off white solid product title compound 21 (11 mg, 0.0252 mmol) was obtained after filtration and air drying at 25° C.

Example 22

Synthesis of 6-(2,6-difluorophenyl)-5-fluoro-N-(4-((tetrahydro-2H-pyran-4-yl)methoxy)pyrimidin-5-yl)picolinamide (22)

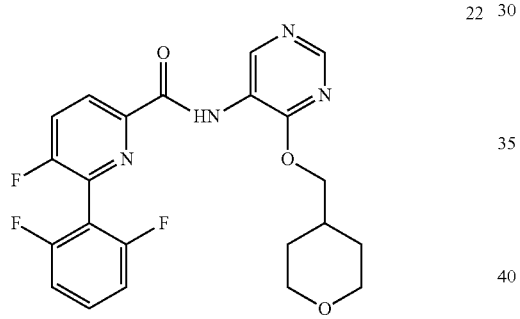

22

Following the procedure described in Example 1, and substituting Compound B1 in Step (1) with (tetrahydro-2H-pyran-4-yl)methanol (B22), the title compound 22 was obtained.

Example 23

Synthesis of 3-amino-6-(2,6-difluorophenyl)-5-fluoro-N-(4-(piperidin-4-ylmethoxy)pyrimidin-5-yl)picolinamide (23)

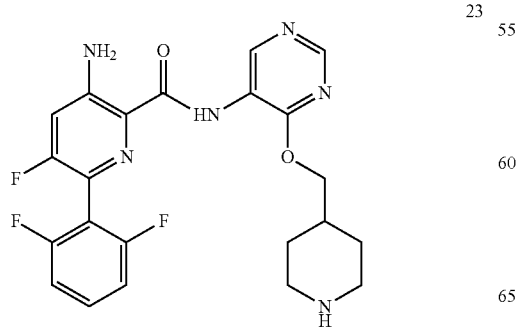

23

Following the procedure described in Example 1, and substituting Compound D1 in Step (2) with 3-amino-6-(2,6-difluorophenyl)-5-fluoropicolinic acid (D2), the title compound 23 was obtained.

Example 24

Synthesis of 3-amino-6-(2,6-difluorophenyl)-5-fluoro-N-(4-(pyrrolidin-3-yloxy)pyrimidin-5-yl)picolinamide (24)

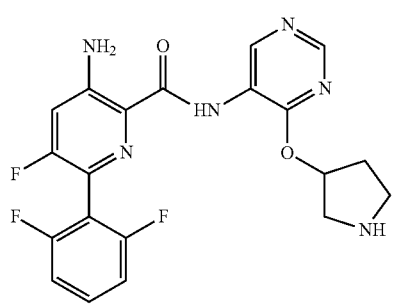

24

Following the procedure described in Example 23, and substituting Compound B1 in Step (1) with B4, the title compound 24 was obtained.

Example 25

Synthesis of 3-amino-6-(2,6-difluorophenyl)-5-fluoro-N-(4-(piperidin-4-yloxy)pyrimidin-5-yl)picolinamide (25)

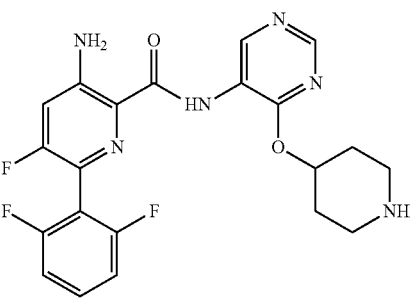

25

Following the procedure described in Example 23, and substituting Compound B1 in Step (1) with B3, the title compound 25 was obtained.

Example 26

Synthesis of 3-amino-N-(4-(azepan-4-yloxy)pyrimidin-5-yl)-6-(2,6-difluorophenyl)-5-fluoropicolinamide (26)

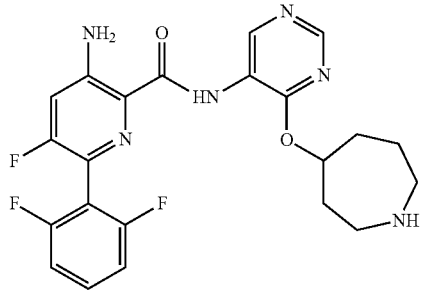

Following the procedure described in Example 23, and substituting Compound B1 in Step (1) with B6, the title compound 26 was obtained.

Example 27

Synthesis of 3-amino-N-(4-(((1r,4r)-4-aminocyclohexyl)oxy)pyrimidin-5-yl)-6-(2,6-difluorophenyl)-5-fluoropicolinamide (27)

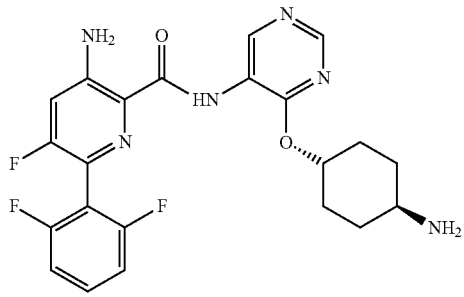

Following the procedure described in Example 23, and substituting Compound B1 in Step (1) with B10, the title compound 27 was obtained.

Example 28

Synthesis of 3-amino-6-(2,6-difluorophenyl)-5-fluoro-N-(4-(pyrrolidin-3-ylmethoxy)pyrimidin-5-yl)picolinamideyl)picolinamide (28)

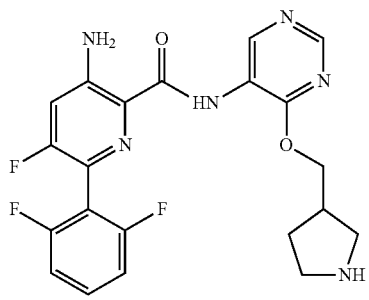

Following the procedure described in Example 23, and substituting Compound B1 in Step (1) with B8, the title compound 28 was obtained.

Example 29

Synthesis of N-(4-((1-amino-3-chloropropan-2-yl)oxy)pyrimidin-5-yl)-6-(2,6-difluorophenyl)-5-fluoropicolinamide (29)

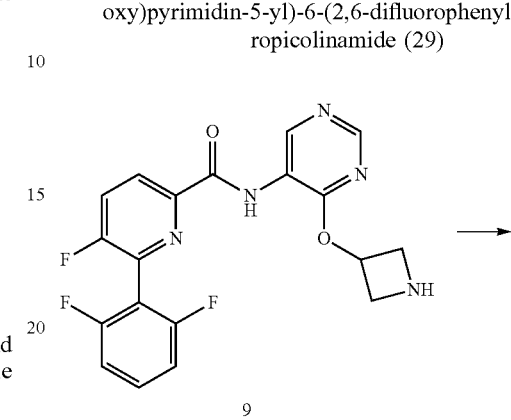

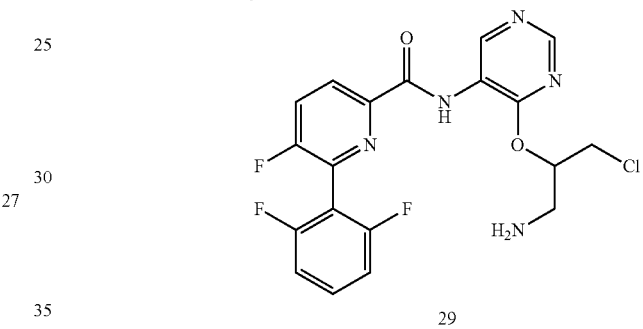

To a solution of 4M HCl in methanol (1 mL) at room temperature was added compound 9 (20 mg, 0.050 mmol). The solution was stirred for 4 hours. The solvent was then removed and the residue was washed with ether and then dried under vacuo to get an off white solid product 29 (21 mg, 0.044 mmol)

Example 30

Synthesis of N-(4-(3-amino-2-(chloromethyl)propoxy)pyrimidin-5-yl)-6-(2,6-difluorophenyl)-5-fluoropicolinamide (30)

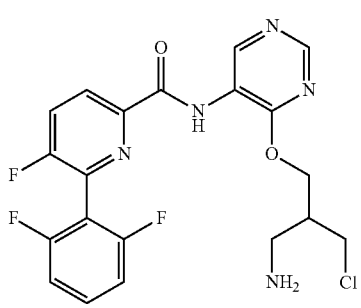

Following the procedure described in Example 29, and substituting Compound 9 with 2, the title compound 30 was obtained.

TABLE I

Analytical data of the compounds described in the examples of the present invention

| Name | NMR | MS |
| --- | --- | --- |
| 6-(2,6-difluorophenyl)-5-fluoro-N-(4-(piperidin-4-ylmethoxy)pyrimidin-5-yl)picolinamide | 1H NMR (400 MHz, DMSO-d6) δ: 1.98 (bs, 2H), 1.20-2.10 (m, 2H), 2.70-2.90 (m, 2H), 2.90-3.70 (m, 5H), 4.32 (bs, 2H), 7.43 (t, 8, 2H), 7.69-7.77 (m, 1H), 8.25 (t, J = 10, 1H), 8.39 (dd, J = 8, 4, 1H), 8.62 (s, 1H), 9.05 (bs, 2H), 9.25 (s, 1H), 10.20 (s, 1H) | 444 (M + 1) |
| N-(4-(azetidin-3-ylmethoxy)pyrimidin-5-yl)-6-(2,6-difluorophenyl)-5-fluoropicolinamide | 1H NMR (400 MHz, DMSO-d6) δ: 1.99 (bs, 1H), 3.60-4.40 (m, 4H), 4.63 (d, J = 6, 2H), 7.41 (t, 8, 2H), 7.46-7.76 (m, 1H), 8.25 (t, J = 10, 1H), 8.39 (dd, J = 8, 4, 1H), 8.63 (s, 1H), 9.05 (bs, 2H), 9.25 (s, 1H), 10.12 (s, 1H) | 416 (M + 1) |
| 6-(2,6-difluorophenyl)-5-fluoro-N-(4-(piperidin-4-yloxy)pyrimidin-5-yl)picolinamide | 1H NMR (400 MHz, DMSO-d6) δ: 1.80-2.00 (m, 2H), 2.20 (bs, 2H), 3.04 (bs, 2H), 3.21 (bs, 2H), 5.12 (bs, 1H), 7.43 (t, 8, 2H), 7.69-7.77 (m, 1H), 8.26 (t, J = 8, 1H), 8.40 (dd, J = 8, 4, 1H), 8.62 (s, 1H), 8.88 (bs, 1H), 9.17 (bs, 1H), 9.35 (s, 1H), 10.21 (s, 1H) | 430 (M + 1) |
| 6-(2,6-difluorophenyl)-5-fluoro-N-(4-(pyrrolidin-3-yloxy)pyrimidin-5-yl)picolinamide | 1H NMR (400 MHz, DMSO-d6) δ: 2.10-2.22 (m, 1H), 2.28-2.31 (m, 1H), 3.00-3.02 (m, 1H), 3.28-3.31 (m, 1H), 3.30-3.34 (m, 2H), 5.71 (bs, 1H), 7.42 (t, J = 8, 2H), 7.69-7.77 (m, 1H), 8.26 (t, J = 8, 1H), 8.38 (dd, J = 10, 4, 1H), 8.64 (s, 1H), 9.11 (bs, 1H), 9.29 (s, 1H), 9.30 (bs, 1H), 10.17 (s, 1H) | 416 (M + 1) |
| 6-(2,6-difluorophenyl)-5-fluoro-N-(4-(piperidin-3-yloxy)pyrimidin-5-yl)picolinamide | 1H NMR (400 MHz, DMSO-d6) δ: 1.39-1.50 (m, 1H), 1.66-1.81 (m, 2H), 2.03-2.08 (m, 1H), 2.21-2.28 (m, 1H), 2.54-2.60 (m, 1H), 2.70-2.76 (m, 2H), 3.06-3.10 (m, 1H), 5.45 (bs, 1H), 7.43 (t, 8, 2H), 7.69-7.77 (m, 1H), 8.26 (t, J = 8, 1H), 8.41 (dd, J = 8, 4, 1H), 8.61 (s, 1H), 8.68 (bs, 1H), 9.17 (bs, 1H), 9.35 (s, 1H), 10.20 (s, 1H) | 430 (M + 1) |
| N-(4-(azepan-4-yloxy)pyrimidin-5-yl)-6-(2,6-difluorophenyl)-5-fluoropicolinamide | 1H NMR (400 MHz, DMSO-d6) δ: 1.68 (m, 1H), 2.06-2.08 (m, 2H), 2.07-2.15 (m, 3H), 2.90-3.00 (m, 4H), 5.41-5.44 (m, 1H), 7.43 (t, 8, 2H), 7.69-7.77 (m, 1H), 8.26 (t, J = 8, 1H), 8.41 (dd, J = 8, 4, 1H), 8.61 (s, 1H), 8.68 (bs, 1H), 9.17 (bs, 1H), 9.35 (s, 1H), 10.20 (s, 1H) | 444 (M + 1) |
| 6-(2,6-difluorophenyl)-5-fluoro-N-(4-(piperidin-3-ylmethoxy)pyrimidin-5-yl)picolinamide | 1H NMR (400 MHz, DMSO-d6) δ: 1.39-1.50 (m, 1H), 1.66-1.81 (m, 2H), 2.03-2.08 (m, 1H), 2.21-2.28 (m, 1H), 2.54-2.60 (m, 1H), 2.70-2.76 (m, 2H), 3.06-3.10 (m, 1H), 4.37 (bs, 2H), 7.42 (t, 8, 2H), 7.45-7.77 (m, 1H), 8.25 (t, J = 8, 1H), 8.40 (dd, J = 8, 4, 1H), 8.63-8.64 (m, 1H), 9.17 (bs, 2H), 9.25 (s, 1H), 10.15 (s, 1H) | 444 (M + 1) |
| 6-(2,6-difluorophenyl)-5-fluoro-N-(4-(pyrrolidin-3-ylmethoxy)pyrimidin-5-yl)picolinamide | 1H NMR (400 MHz, DMSO-d6) δ: 1.67-1.74 (m, 1H), 2.08-2.17 (m, 1H), 2.71-2.78 (m, 1H), 2.83-2.97 (m, 2H), 3.02-3.08 (m, 1H), 3.16-3.21 (m, 1H), 4.42-4.45 (m, 2H), 7.44 (t, 8, 2H), 7.71-7.77 (m, 1H), 8.26 (t, J = 8, 1H), 8.39 (dd, J = 8, 4, 1H), 8.62 (s, 1H), 9.07 (bs, 1H), 9.15 (bs, 1H), 9.28 (s, 1H), 10.12 (s, 1H) | 430 (M + 1) |
| N-(4-(azetidin-3-yloxy)pyrimidin-5-yl)-6-(2,6-difluorophenyl)-5-fluoropicolinamide | 1H NMR (400 MHz, DMSO-d6) δ: 4.00-4.10 (m, 2H), 4.43-4.51 (m, 2H), 5.40-5.50 (m, 1H), 7.40 (t, 8, 2H), 7.70-7.77 (m, 1H), 8.26 (t, J = 8, 1H), 8.40 (dd, J = 8, 4, 1H), 8.61 (s, 1H), 9.07 (bs, 1H), 9.25 (bs, 1H), 9.27 (s, 1H), 10.17 (s, 1H) | 402 (M + 1) |
| N-(4-(((1r,4r)-4-aminocyclohexyl)oxy)pyrimidin-5-yl)-6-(2,6-difluorophenyl)-5-fluoropicolinamide | 1H NMR (400 MHz, DMSO) δ: 1.09-1.51 (m, 2H), 1.65-1.69 (m, 2H), 1.98-2.02 (m, 2H), 2.20-2.23 (m, 2H), 2.85-2.90 (m, 1H), 5.35-5.41 (m, 1H), 7.22 (bs, 3H), 7.40 (t, 8, 2H), 7.70-7.77 (m, 1H), 8.26 (t, J = 8, 1H), 8.40 (dd, J = 8, 4, 1H), 8.61 (s, 1H), 9.26 (s, 1H), 10.18 (s, 1H) | 444 (M + 1) |
| N-(4-((3-aminocyclohexyl)oxy)pyrimidin-5-yl)-6-(2,6-difluorophenyl)-5-fluoropicolinamide | 1H NMR (400 MHz, DMSO) δ: 1.10-1.50 (m, 5H), 2.60-2.80 (m, 3H), 3.0-3.50 (m, 1H), 3.95-4.05 (m, 0.7H), 4.4 (bs, 0.3H), 7.22 (bs, 3H), 7.39 (t, 8, 2H), 7.70-7.77 (m, 1H), 8.26 (t, J = 8, 1H), 8.40 (dd, J = 8, 4, 1H), 8.61 (s, 1H), 9.26 (s, 1H), 10. 25 (s, 1H) | 444 (M + 1) |
| N-(4-(3-aminopropoxy)pyrimidin-5-yl)-6-(2,6-difluorophenyl)-5-fluoropicolinamide | 1H NMR (400 MHz, DMSO-d6) δ: 1.84 (bs, 2H), 2.80 (bs, 2H), 4.21 (bs, 2H), 7.22 (bs, 3H), 7.43 (t, J = 8, 2H), 7.65 (d, J = 6, 1H), 7.40 (t, 8, 2H), 7.70-7.77 (m, 1H), 8.26 (t, J = 8, 1H), 8.40 (dd, J = 8, 4, 1H), 8.61 (s, 1H), 9.26 (s, 1H), 10.20 (s, 1H) | 444 (M + 1) |
| 6-(2,6-difluorophenyl)-5-fluoro-N-(4-(3-(methylamino)propoxy)pyrimidin-5-yl)picolinamide | 1H NMR (400 MHz, DMSO-d6) δ: 1.85 (bs, 2H), 2.80 (bs, 2H), 2.90 (s, 3H), 4.22 (bs, 2H), 7.42 (t, 8, 2H), 7.45-7.77 (m, 1H), 8.25 (t, J = 8, 1H), 8.40 (dd, J = 8, 4, 1H), 8.63 (s, 1H), 9.17 (bs, 2H), 9.25 (s, 1H), 10.16 (s, 1H) | 418 (M + 1) |

TABLE I-continued

Analytical data of the compounds described in the examples of the present invention

| Name | NMR | MS |
| --- | --- | --- |
| 6-(2,6-difluorophenyl)-N-(4-(3-(dimethylamino)propoxy)pyrimidin-5-yl)-5-fluoropicolinamide | 1H NMR (400 MHz, DMSO-d6) δ: 1.85 (bs, 2H), 2.79 (bs, 2H), 2.92 (s, 6H), 4.21 (bs, 2H), 7.42 (t, 8, 2H), 7.45-7.77 (m, 1H), 8.25 (t, J = 8, 1H), 8.40 (dd, J = 8, 4, 1H), 8.63 (s, 1H), 9.17 (bs, 1H), 9.26 (s, 1H), 10.20 (s, 1H) | 432 (M + 1) |
| N-(4-(4-aminobutoxy)pyrimidin-5-yl)-6-(2,6-difluorophenyl)-5-fluoropicolinamide | 1H NMR (400 MHz, DMSO-d6) δ: 1.50-1.57 (m, 2H), 1.75-1.78 (m, 2H), 2.81-2.84 (m, 2H), 4.21 (t, J = 6, 2H), 7.22 (bs, 3H), 7.43 (t, J = 8, 2H), 7.65 (d, J = 6, 1H), 7.40 (t, 8, 2H), 7.70-7.77 (m, 1H), 8.26 (t, J = 8, 1H), 8.40 (dd, J = 8, 4, 1H), 8.61 (s, 1H), 9.26 (s, 1H), 10.20 (s, 1H) | 418 (M + 1) |
| 6-(2,6-difluorophenyl)-5-fluoro-N-(4-(4-(methylamino)butoxy)pyrimidin-5-yl)picolinamide | 1H NMR (400 MHz, DMSO-d6) δ: 1.49-1.60 (m, 2H), 1.79-1.84 (m, 2H), 2.81-2.82 (m, 2H), 2.92 (s, 3H), 4.30 (t, J = 6, 2H), 7.42 (t, 8, 2H), 7.45-7.77 (m, 1H), 8.25 (t, J = 8, 1H), 8.40 (dd, J = 8, 4, 1H), 8.63 (s, 1H), 9.10 (bs, 2H), 9.26 (s, 1H), 10.13 (s, 1H) | 432 (M + 1) |
| 6-(2,6-difluorophenyl)-5-fluoro-N-(4-(3-hydroxypropoxy)pyrimidin-5-yl)picolinamide | 1H NMR (400 MHz, DMSO-d6) δ: 1.96-1.98 (m, 2H), 3.60-3.63 (m, 2H), 4.26 (t, J = 6, 2H), 4.56 (bs, 1H), 7.42 (t, 8, 2H), 7.45-7.77 (m, 1H), 8.26 (t, J = 8, 1H), 8.41 (dd, J = 8, 4, 1H), 8.62 (s, 1H), 9.25 (s, 1H), 10.25 (s, 1H) | 405 (M + 1) |
| 6-(2,6-difluorophenyl)-5-fluoro-N-(4-(3-hydroxybutoxy)pyrimidin-5-yl)picolinamide | 1H NMR (400 MHz, DMSO-d6) δ: 1.07 (s, 3H), 1.69-1.85 (m, 2H), 3.45-3.55 (m, 1H), 4.15-4.25 (m, 2H), 4.58 (s, 1H), 7.42 (t, 8, 2H), 7.45-7.77 (m, 1H), 8.26 (t, J = 8, 1H), 8.42 (dd, J = 8, 4, 1H), 8.62 (s, 1H), 9.25 (s, 1H), 10.21 (s, 1H) | 419 (M + 1) |
| 6-(2,6-difluorophenyl)-5-fluoro-N-(4-(4-hydroxybutoxy)pyrimidin-5-yl)picolinamide | 1H NMR (400 MHz, DMSO-d6) δ: 1.45-1.52 (m, 2H), 1.74-1.78 (m, 2H), 3.35-3.45 (m, 2H), 4.22 (t, J = 6, 2H), 4.43 (bs, 1H), 7.42 (t, 8, 2H), 7.45-7.77 (m, 1H), 8.26 (t, J = 8, 1H), 8.41 (dd, J = 8, 4, 1H), 8.62 (s, 1H), 9.25 (s, 1H), 10.25 (s, 1H) | 419 (M + 1) |
| 6-(2,6-difluorophenyl)-5-fluoro-N-(4-((4-hydroxy-4-methylpentyl)oxy)pyrimidin-5-yl)picolinamide | 1H NMR (400 MHz, DMSO-d6) δ: 1.11 (s, 6H), 1.40-1.47 (m, 2H), 1.69-1.80 (m, 2H), 4.21 (t, J = 7, 2H), 7.42 (t, 8, 2H), 7.45-7.75 (m, 1H), 8.26 (t, J = 8, 1H), 8.43 (dd, J = 8, 4, 1H), 8.62 (s, 1H), 9.25 (s, 1H), 10.20 (s, 1H) | 447 (M + 1) |
| 6-(2,6-difluorophenyl)-N-(4-(3,4-dihydroxybutoxy)pyrimidin-5-yl)-5-fluoropicolinamide | 1H NMR (400 MHz, DMSO-d6) δ: 1.92-2.10 (m, 2H), 3.29 (s, 1H), 3.70 (s, 2H), 4.15-4.35 (m, 2H), 4.50 (s, 1H), 4.65 (d, J = 5.04, 1H), 7.42 (t, 8, 2H), 7.45-7.77 (m, 1H), 8.26 (t, J = 8, 1H), 8.42 (dd, J = 8, 4, 1H), 8.62 (s, 1H), 9.25 (s, 1H), 10.13 (s, 1H) | 435 (M + 1) |
| 6-(2,6-difluorophenyl)-5-fluoro-N-(4-((tetrahydro-2H-pyran-4-yl)methoxy)pyrimidin-5-yl)picolinamide | 1H NMR (400 MHz, DMSO-d6) δ: 1.70-1.85 (m, 1H), 2.20-2.38 (m, 2H), 2.59-2.69 (m, 2H), 3.74-3.85 (m, 2H), 3.97-4.05 (m, 4H), 7.42 (t, 8, 2H), 7.45-7.75 (m, 1H), 8.26 (t, J = 8, 1H), 8.42 (dd, J = 8, 4, 1H), 8.62 (s, 1H), 9.25 (s, 1H), 10.19 (s, 1H) | 445 (M + 1) |
| 3-amino-6-(2,6-difluorophenyl)-5-fluoro-N-(4-(piperidin-4-ylmethoxy)pyrimidin-5-yl)picolinamide | 1H NMR (400 MHz, DMSO-d6) δ 1.68-1.85 (m, 1H), 2.23-2.38 (m, 2H), 2.59-2.69 (m, 2H), 3.74-3.85 (m, 2H), 3.97-4.05 (m, 4H), 7.20-7.31 (m, 3H), 7.34 (d, 1H), 7.36 (bs, 2H), 7.50-7.60 (m, 1H), 8.43 (dd, J = 8, 4, 1H), 8.81 (s, 1H), 9.13 (bs, 2H), 10.24 (s, 1H) | 459 (M + 1) |
| 3-amino-6-(2,6-difluorophenyl)-5-fluoro-N-(4-(pyrrolidin-3-yloxy)pyrimidin-5-yl)picolinamide | 1H NMR (400 MHz, DMSO-d6) δ: 2.05-2.20 (m, 1H), 2.28-2.31 (m, 1H), 3.00-3.02 (m, 1H), 3.28-3.31 (m, 1H), 3.30-3.34 (m, 2H), 5.68 (bs, 1H), 7.20-7.31 (m, 3H), 7.35 (d, 1H), 7.36 (bs, 2H), 7.52-7.62 (m, 1H), 8.44 (dd, J = 8, 4, 1H), 8.83 (s, 1H), 9.10 (bs, 2H), 10.14 (s, 1H) | 431 (M + 1) |
| 3-amino-6-(2,6-difluorophenyl)-5-fluoro-N-(4-(piperidin-4-yloxy)pyrimidin-5-yl)picolinamide | 1H NMR (400 MHz, DMSO-d6) δ: 1.75-1.95 (m, 2H), 2.20 (bs, 2H), 3.04 (bs, 2H), 3.21 (bs, 2H), 5.12 (bs, 1H), 7.44 (t, 8, 2H), 7.71-7.77 (m, 1H), 8.26 (t, J = 8, 1H), 8.40 (dd, J = 8, 4, 1H), 8.62 (s, 1H), 8.88 (bs, 1H), 9.25 (bs, 1H), 9.37 (s, 1H), 10.23 (s, 1H) | 445 (M + 1) |
| 3-amino-N-(4-(azepan-4-yloxy)pyrimidin-5-yl)-6-(2,6-difluorophenyl)-5-fluoropicolinamide | 1H NMR (400 MHz, DMSO-d6) δ: 1.68 (m, 1H), 2.06-2.08 (m, 2H), 2.05-2.15 (m, 3H), 2.90-3.00 (m, 4H), 5.41-5.44 (m, 1H), 7.44 (t, 8, 2H), 7.71-7.77 (m, 1H), 8.26 (t, J = 8, 1H), 8.40 (dd, J = 8, 4, 1H), 8.62 (s, 1H), 8.89 (bs, 1H), 9.18 (bs, 1H), 9.35 (s, 1H), 10.13 (s, 1H) | 459 (M + 1) |
| 3-amino-N-(4-(((1r,4r)-4-aminocyclohexyl)oxy)pyrimidin-5-yl)-6-(2,6-difluorophenyl)-5-fluoropicolinamide | 1H NMR (400 MHz, DMSO-d6) δ: 1.15-1.31 (m, 2H), 1.45-1.57 (m, 2H), 1.78-1.91 (m, 2H), 2.05-2.17 (m, 2H), 3.10 (bs, 1H), 4.90 (bs, 1H), 7.44 (t, 8, 2H), 7.71-7.76 (m, 1H), 8.26 (t, J = 8, 1H), 8.41 (dd, J = 8, 4, 1H), 8.62 (s, 1H), 9.18 (bs, 2H), 9.35 (s, 1H), 10.19 (s, 1H) | 459 (M + 1) |

TABLE I-continued

Analytical data of the compounds described in the examples of the present invention

| Name | NMR | MS |
|---|---|---|
| 3-amino-6-(2,6-difluorophenyl)-5-fluoro-N-(4-(pyrrolidin-3-ylmethoxy)pyrimidin-5-yl)picolinamideyl)picolinamide | 1HNMR (400 MHz, DMSO-d6) δ: 2.02-2.18 (m, 1H), 2.28-2.30 (m, 1H), 3.00-3.02 (m, 1H), 3.28-3.31 (m, 1H), 3.30-3.34 (m, 2H), 5.71 (bs, 1H), 7.22-7.30 (m, 3H), 7.34 (d, 1H), 7.36 (bs, 2H), 7.50-7.60 (m, 1H), 8.42 (dd, J = 8, 4, 1H), 8.82 (s, 1H), 9.17 (bs, 2H), 10.26 (s, 1H) | 445 (M + 1) |
| N-(4-((1-amino-3-chloropropan-2-yl)oxy)pyrimidin-5-yl)-6-(2,6-difluorophenyl)-5-fluoropicolinamide | 1H NMR (400 MHz, CDCl3) δ: 3.14 (dd, J = 12, 8, 1H), 3.23 (dd, J = 10, 4, 1H), 3.78 (d, J = 8, 2H), 4.15-4.31 (m, 1H), 7.40 (t, 8, 2H), 7.45-7.75 (m, 1H), 8.27 (t, J = 8, 1H), 8.40 (dd, J = 8, 4, 1H), 8.60 (s, 1H), 9.20 (s, 1H), 10.05 (s, 1H) | 438 (M + 1) |
| N-(4-(3-amino-2-(chloromethyl)propoxy)pyrimidin-5-yl)-6-(2,6-difluorophenyl)-5-fluoropicolinamide | 1H NMR (400 MHz, CDCl3) δ: 2.25-2.70 (m, 2H), 2.90-3.05 (m, 1H), 3.65 (s, 1H), 3.79 (d, J = 8, 2H), 4.20-4.40 (m, 2H), 7.42 (t, 8, 2H), 7.47-7.77 (m, 1H), 8.26 (t, J = 8, 1H), 8.41 (dd, J = 8, 4, 1H), 8.62 (s, 1H), 9.19 (s, 1H), 10.00 (s, 1H) | 452 (M + 1) |

Example 31

The biochemical assays used to test the activities of the compounds of the present invention and their results.

In the present invention, the PIM activities of the compounds were tested by BioDuro (Building E, No. 29 Life Science Park Road, Changing District, Beijing, 102206, P.R. China). The method used for testing is PIM Kinase Activity Assay-IMAP Fluorescence Polarization Assay PIM Kinase Activity Assay-IMAP Fluorescence Polarization Assay 1. Principle PIM Is a serine/threonine protein kinase, they can phosphorylate 5-FAM labeled small peptide substrates. Fluorescence polarization is less for non-phosphorylated substrates since that can not bind to the binder (metal binding nanoparticles). On the other hand, fluorescence polarization is more for phosphorylated substrates since that can bind to the binder. The level of 5-FAM labeled small peptide substrates phosphorylation reflects the activities of PIM kinase. By measuring their ability of inhibiting PIM kinase of the compounds of the present invention, their activities of inhibiting PIM kinases can be determined.

2. Instrument

EnVision (PerkinElmer, Waltham, Mass.)

3. Reagents and 384 Well Plates

PIM1 (Millipore Cat. #14-573) (Millipore Corporation, Billerica, Mass.)

PIM2 (Millipore Cat. #14-607) (Millipore Corporation, Billerica, Mass.)

5-FAM labeled peptide (5-FAM-RSRHSSYPAGT, AnaSpec Cat. #63801) (AnaSpec Inc., Fremont Calif.)

IMAP FP Screening Express kit (IMAP FP Screening kit) (Molecular Devices Cat. # R8127) (Molecular Devices, Sunnyvale, Calif.)

IMAP Progressive binding reagent
IMAP Progressive binding buffer A (5×)
IMAP Progressive binding buffer B (5×)
384-well black plate (Corning Cat. #3573) (Corning, Midland Mich.)

4. Assay Buffer

Tris-HCl (pH 7.2): 10 mM
$MgCl_2$: 10 mM
Triton X-100: 0.01%
DTT: 2 mM

5. Procedure a) 10 mM compound stock solution is diluted to appropriate concentration with 100% DMSO, then diluted 10 fold to targeted concentration with test butter to keep DMSO concentration at 10% b) Assay volume 10 ul:

1 ul of compound solution and 4 ul of enzyme (PIM-1 final concentration 0.025 nM, PIM-2 concentration 3 nM) is incubated at 23° C. for 15 min, 2.5 ul ATP (for PIM-1 and PIM-2, the final ATP concentrations are 30 uM and 5 uM respectively) 2.5 ul 5-FAM labeled peptide (final concentration 100 nM) was added to start the reaction. The reaction is run at 23° C. for 60 min. DMSO is used in place of compound stock solution as maximum reference and assay buffer is used in place of enzyme as minimum reference.

c) add 30 ul IMAP binding reagent (containing 75% IMAP Buffer A, 25% IMAP Buffer B, 1/600 dilution of beads) to stop the reaction, incubated at room temperature for 60 min d) Measure fluorescence polarization, excitation wavelength: 485 nm, emission wavelength 530 nm.

6. Data process $IC_{50}$ values were calculated using Graphpad Prism®.

PIM kinase assays showed that all 30 compounds in Example 1 through 30 can significantly inhibit the PIM-1, PIM-2 and PIM-3 activities. The $IC_{50}$ of these compounds range from 0.1 nM to 50 nM.

I claim:

1. A compound having a structure of Formula II:

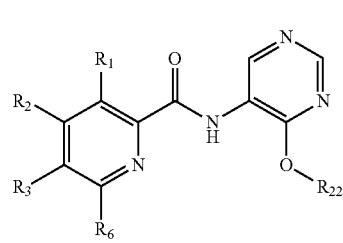

II wherein $R_1$ is a hydrogen, $-NHR_4$, a halogen, a hydroxyl, an alkyl, a cyano, or a nitro;

$R_2$ is a hydrogen, $-NHR_5$, a halogen, a hydroxyl, a substituted or unsubstituted alkyl, an alkenyl, an alkynyl, an alkoxyl, a cycloalkyl, an amino, a cyano, or a nitro;

$R_3$ is —$NHR_5$, a halogen, a hydroxyl, a substituted or unsubstituted alkyl, an alkenyl, an alkynyl, an alkoxyl, a cycloalkyl, an amino, a cyano, or a nitro;

$R_4$ is a hydrogen, —C(=O)—$R_5$, a substituted or unsubstituted alkyl, a cycloalkyl, a heterocyclyl, an aryl, or a heteroaryl;

$R_5$ is a substituted or unsubstituted alkyl, alkenyl, alkynyl, alkoxyl, cycloalkyl, amino, or substituted amino;

$R_6$ is a substituted or unsubstituted aryl, heteroaryl, cycloalkyl, wherein each substituted $R_6$ group is substituted with up to four substituents that is a halogen, a cyano, an amino, a $C_{1-4}$ alkyl, a $C_{3-6}$ cycloalkyl, an alkoxyl, a nitro, a carboxy, a carbonyl, a carboalkoxy, or an aminocarboxy;

$R_{22}$ is an optionally substituted $C_1$-$C_8$ hydrocarbon group or a group having a formula:

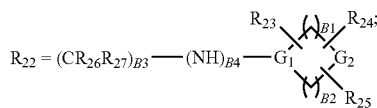

wherein each of $R_{23}$, $R_{24}$, $R_{25}$ is independently selected from a H, a halogen, $OR_{15}$, $NR_{16}R_{17}$, C(=O)N$R_{18}R_{19}$, or an optionally substituted $C_1$-$C_8$ hydrocarbon group; or $R_{23}$, $R_{24}$ and $R_{25}$, together with atoms to which they are attached, are joined together to form a chain so that the ring to which they are attached is a substituted $C_6$-$C_{14}$ membered spiral ring, a bicyclic ring, or a fused ring group;

$G_1$ is CH or N;
$G_2$ is $NR_{28}$, $CHR_{29}$, or O;
B1 and B2 each independently represents 0, 1, 2, or 3;
B3 is 0, 1, or 2;
B4 is 0 or 1;
each of $R_{16}$, $R_{17}$, $R_{18}$, $R_{19}$, $R_{26}$ and $R_{27}$ is independently selected from a H or an optionally substituted $C_1$-$C_8$ hydrocarbon group;

$R_{28}$ is H, an optionally substituted hydrocarbon group, an optionally substituted cyclic hydrocarbon group, an optionally substituted heterocyclic hydrocarbon group, C(=O)$R_{30}$, C(=O)O$R_{30}$, or C(=O)NH$R_{30}$;

$R_{29}$ is OH, NH$R_{30}$, C(=O)O$R_{30}$, or C(=O)NH$R_{30}$; and
$R_{30}$ is H or an optionally substituted $C_1$-$C_8$ hydrocarbon group, or a stereoisomer, tautomer, or a pharmaceutically acceptable salt thereof.

2. The compound according to claim 1, wherein $R_{22}$ is a substituted or unsubstituted cyclobutyl, cyclopentyl, cyclohexyl, cycloheptyl, azetidyl, pyrrolidinyl, piperidinyl, azepanyl, oxetyl, tetrahydrofuryl, or tetrahydropyranyl group;

$R_{22}$ group is substituted with up to three substitutents that is an amino, a hydroxy, a methyl, an ethyl, or a methoxy;
$R_1$ is a hydrogen, an amino, or a fluoro;
$R_2$ is a hydrogen, a halogen, or a methyl;
$R_3$ is a halogen; and
$R_6$ is a substituted or unsubstituted phenyl, wherein the substituted phenyl group is substituted with up to three substituents that is a hydrogen, a cyano, a nitro, a halogen, a hydroxyl, an amino, an alkoxy, a substituted amino, an alkyl, or a cycloalkyl.

3. The compound according to claim 2, wherein $R_{22}$ is a substituted or unsubstituted cyclohexyl, cycloheptyl, pyrrolidinyl, piperidinyl, or azepanyl group;

when $R_{22}$ is a substituted group, it is substituted with up to three substitutents that is an amino, a hydroxy, or a methyl;
$R_1$ is a hydrogen, an amino, or a fluoro;
$R_2$ is a hydrogen, a halogen, or a methyl;
$R_3$ is a halogen; and
$R_6$ is a substituted or unsubstituted phenyl, and the substituted phenyl group is substituted with up to three substituents that is a hydrogen, a cyano, a nitro group, a halogen, or a hydroxyl.

4. The compound according to claim 1, wherein $R_{22}$ is a substituted or unsubstituted cyclobutylmethyl, cyclopentylmethyl, cyclohexylmethyl, cycloheptylmethyl, azetidylmethyl, pyrrolidinylmethyl, piperidinylmethyl, azepanylmethyl, oxetylmethyl, tetrahydrofurylmethyl, or tetrahydropyranylmethyl group;

$R_{22}$ group is substituted with up to three substitutents that is an amino, a hydroxy, a methyl, an ethyl, or a methoxy;
$R_1$ is a hydrogen, an amino, or a fluoro;
$R_2$ is a hydrogen, a halogen, or a methyl;
$R_3$ is a halogen; and
$R_6$ is a substituted or unsubstituted phenyl, and the substituted phenyl is substituted with up to three substituents that is a hydrogen, a cyano, a nitro, a halogen, a hydroxyl, an amino, an alkoxy, a substituted amino, an alkyl, or a cycloalkyl.

5. The compound according to claim 4, wherein $R_{22}$ is a substituted or unsubstituted cyclohexylmethyl, pyrrolidinylmethyl, piperidinylmethyl, or azepanylmethyl group, the substituted $R_{22}$ group is substituted with up to three substitutents that is an amino, a hydroxy, or a methyl;
$R_1$ is a hydrogen, an amino, or a fluoro;
$R_2$ is a hydrogen, a halogen, or a methyl;
$R_3$ is a halogen; and
$R_6$ is a substituted or unsubstituted phenyl, and the substituted phenyl is substituted with up to three substituents that is a hydrogen, a cyano, or a halogen.

6. The compound according to claim 4, wherein $R_{22}$ is a substituted $C_2$-$C_5$ alkyl,
the substituted $R_{22}$ group is substituted at any position on substituent with up to four substitutents that is an amino, an alkylamino, a hydroxy, a halogen, a methyl, an ethyl, a halogenated methyl, or a halogenated ethyl group;
$R_1$ is a hydrogen, an amino, or a fluoro;
$R_2$ is a hydrogen;
$R_3$ is a halogen; and
$R_6$ is a substituted or unsubstituted phenyl, and the substituted phenyl is substituted with up to three substituents that is a hydrogen, a methyl, or a halogen.

7. The compound according to claim 3, wherein $R_1$ is a hydrogen or an amino; $R_2$ is hydrogen; $R_3$ is a halogen; $R_6$ is a substituted or unsubstituted phenyl, and the substituted phenyl is substituted with up to three substituents that is a hydrogen or a halogen.

8. The compound according to claim 5, wherein $R_1$ is a hydrogen or an amino; $R_2$ is hydrogen; $R_3$ is a halogen; $R_6$ is a substituted or unsubstituted phenyl, and the substituted phenyl is substituted with up to three substituents that is a hydrogen or a halogen.

9. A compound according to claim 1, wherein the compound is 6-(2,6-difluorophenyl)-5-fluoro-N-(4-(piperidin-4-ylmethoxy)pyrimidin-5-yl)picolinamide; N-(4-(azetidin-3-ylmethoxy)pyrimidin-5-yl)-6-(2,6-difluorophenyl)-5-fluoropicolinamide; 6-(2,6-difluorophenyl)-5-fluoro-N-(4-(piperidin-4-yloxy)pyrimidin-5-yl)picolinamide; 6-(2,6- difluorophenyl)-5-fluoro-N-(4-(pyrrolidin-3-yloxy) pyrimidin-5-yl)picolinamide; 6-(2,6-difluorophenyl)-5-fluoro-N-(4-(piperidin-3-yloxy)pyrimidin-5-yl) picolinamide; N-(4-(azocan-4-yloxy)pyrimidin-5-yl)-6-(2,6-difluorophenyl)-5-fluoropicolinamide; 6-(2,6-difluorophenyl)-5-fluoro-N-(4-(piperidin-3-ylmethoxy) pyrimidin-5-yl)picolinamide; 6-(2,6-difluorophenyl)-5-fluoro-N-(4-(pyrrolidin-3-ylmethoxy)pyrimidin-5-yl) picolinamide; N-(4-(azetidin-3-yloxy)pyrimidin-5-yl)-6-(2,6-difluorophenyl)-5-fluoropicolinamide; N-(4-(((1r,4r)-4-aminocyclohexyl)oxy)pyrimidin-5-yl)-6-(2,6-difluorophenyl)-5-fluoropicolinamide; N-(4-((3-aminocyclohexyl)oxy)pyrimidin-5-yl)-6-(2,6-difluorophenyl)-5-fluoropicolinamide; N-(4-(3-aminopropoxy)pyrimidin-5-yl)-6-(2,6-difluorophenyl)-5-fluoropicolinamide; 6-(2,6-difluorophenyl)-5-fluoro-N-(4-(3-(methylamino)propoxy)pyrimidin-5-yl)picolinamide; 6-(2,6-difluorophenyl)-N-(4-(3-(dimethylamino)propoxy) pyrimidin-5-yl)-5-fluoropicolinamide; N-(4-(4-aminobutoxy)pyrimidin-5-yl)-6-(2,6-difluorophenyl)-5-fluoropicolinamide; 6-(2,6-difluorophenyl)-5-fluoro-N-(4-(4-(methylamino)butoxy)pyrimidin-5-yl)picolinamide; 6-(2,6-difluorophenyl)-5-fluoro-N-(4-(3-hydroxypropoxy) pyrimidin-5-yl)picolinamide; 6-(2,6-difluorophenyl)-5-fluoro-N-(4-(3-hydroxybutoxy)pyrimidin-5-yl) picolinamide; 6-(2,6-difluorophenyl)-5-fluoro-N-(4-(4-hydroxybutoxy)pyrimidin-5-yl)picolinamide; 6-(2,6-difluorophenyl)-5-fluoro-N-(4-((4-hydroxy-4-methylpentyl)oxy)pyrimidin-5-yl)picolinamide; 6-(2,6-difluorophenyl)-N-(4-(3,4-dihydroxybutoxy)pyrimidin-5-yl)-5-fluoropicolinamide; N-(4-(3-amino-4-hydroxybutoxy) pyrimidin-5-yl)-6-(2,6-difluorophenyl)-5-fluoropicolinamide; 6-(2,6-difluorophenyl)-5-fluoro-N-(4-((tetrahydro-2H-pyran-4-yl)methoxy)pyrimidin-5-yl) picolinamide; 3-amino-6-(2,6-difluorophenyl)-5-fluoro-N-(4-(piperidin-4-ylmethoxy)pyrimidin-5-yl)picolinamide; 3-amino-6-(2,6-difluorophenyl)-5-fluoro-N-(4-(pyrrolidin-3-yloxy)pyrimidin-5-yl)picolinamide; 3-amino-6-(2,6-difluorophenyl)-5-fluoro-N-(4-(piperidin-4-yloxy)pyrimidin-5-yl)picolinamide; 3-amino-N-(4-(azepan-4-yloxy)pyrimidin-5-yl)-6-(2,6-difluorophenyl)-5-fluoropicolinamide; 3-amino-N-(4-(((1r,4r)-4-aminocyclohexyl)oxy)pyrimidin-5-yl)-6-(2,6-difluorophenyl)-5-fluoropicolinamide; 3-amino-6-(2,6-difluorophenyl)-5-fluoro-N-(4-(pyrrolidin-3-ylmethoxy) pyrimidin-5-yl)picolinamideyl)picolinamide; N-(4-((1-amino-3-chloropropan-2-yl)oxy)pyrimidin-5-yl)-6-(2,6-difluorophenyl)-5-fluoropicolinamide; or N-(4-(3-amino-2-(chloromethyl)propoxy)pyrimidin-5-yl)-6-(2,6-difluorophenyl)-5-fluoropicolinamide.

10. A method for using the compound of claim 1, comprising administering to a subject in need of a treatment a therapeutically effective amount of the compound as described in claim 1, wherein the treatment is for treating chronic lymphocytic leukemia, acute lymphoblastic leukemia, acute myeloid leukemia, chronic myelogenous leukemia, non-Hodgkin's lymphoma, multiple myeloma, pancreatic cancers, prostate cancers, liver cancers, gastric cancer, bladder cancer, and inflammatory bowel disease.

11. A method for using the compound of claim 9, comprising administering to a subject in need of a treatment a therapeutically effective amount of the compound as described in claim 9, wherein the treatment is for treating chronic lymphocytic leukemia, acute lymphoblastic leukemia, acute myeloid leukemia, chronic myelogenous leukemia, non-Hodgkin's lymphoma, multiple myeloma, pancreatic cancers, prostate cancers, liver cancers, gastric cancer, bladder cancer, and inflammatory bowel disease.

12. A pharmaceutical composition comprising the compound of claim 1 as an active pharmaceutical ingredient and a pharmaceutically acceptable carrier or adjuvant.

13. A pharmaceutical composition comprising the compound of claim 9 as an active pharmaceutical ingredient and a pharmaceutically acceptable carrier or adjuvant.

14. A pharmaceutical composition comprising the compound of claim 1 in combination with an additional chemotherapeutic agent.

* * * * *